United States Patent [19]

Sakurai

[11] Patent Number: 4,965,532

[45] Date of Patent: Oct. 23, 1990

[54] CIRCUIT FOR DRIVING ULTRASONIC TRANSDUCER

[75] Inventor: Tomohisa Sakurai, Hachioji, Japan

[73] Assignee: Olympus Optical Co., Ltd., Tokyo, Japan

[21] Appl. No.: 365,826

[22] Filed: Jun. 14, 1989

[30] Foreign Application Priority Data

Jun. 17, 1988 [JP] Japan .................................. 63-149415
Apr. 7, 1989 [JP] Japan ..................................... 1-86944
May 15, 1989 [JP] Japan ................................... 1-120748

[51] Int. Cl.$^5$ ........................ H03L 7/10; H03L 7/12; G05D 19/02
[52] U.S. Cl. ........................................ 331/4; 331/65; 331/158; 310/316
[58] Field of Search ........................ 331/1 A, 4, 14, 18, 331/25, 65, 158; 310/314, 316, 317, 318, 319

[56] References Cited

U.S. PATENT DOCUMENTS

| | | | |
|---|---|---|---|
| 4,275,363 | 6/1981 | Mishiro et al. | 331/4 |
| 4,587,958 | 5/1986 | Noguchi et al. | 310/316 X |
| 4,724,401 | 2/1988 | Hogge, Jr. et al. | 331/4 |
| 4,754,186 | 6/1988 | Choperena et al. | 310/316 |
| 4,879,528 | 11/1989 | Gotanda | 331/4 |

*Primary Examiner*—David Mis
*Attorney, Agent, or Firm*—Stevens, Davis, Miller & Mosher

[57] ABSTRACT

Circuit for use in a surgical operation including a phase lock loop having a voltage controlled oscillator, and a phase comparator for comparing a phase of a voltage of a driving signal and a phase of a signal representing the vibration phase of the ultrasonic transducer to derive a phase difference therebetween which is applied to the voltage controlled oscillator as a frequency control voltage such that the driving signal is phase-locked with a resonance frequency of the ultrasonic transducer, the improvement being characterized in that during a start period, a reference signal having a frequency which is increased monotonously is applied to the phase comparator such that the frequency of the driving signal is increased until the driving signal is phase-locked with the vibration phase of the ultrasonic transducer vibrating at the resonance frequency. After the phase-lock condition has been attained, the signal representing the vibration phase of the ultrasonic transducer is applied to the phase comparator instead of the reference signal.

41 Claims, 24 Drawing Sheets

FIG.8A θref
FIG.8B θv
FIG.8C θI

FIG_10

FIG_15

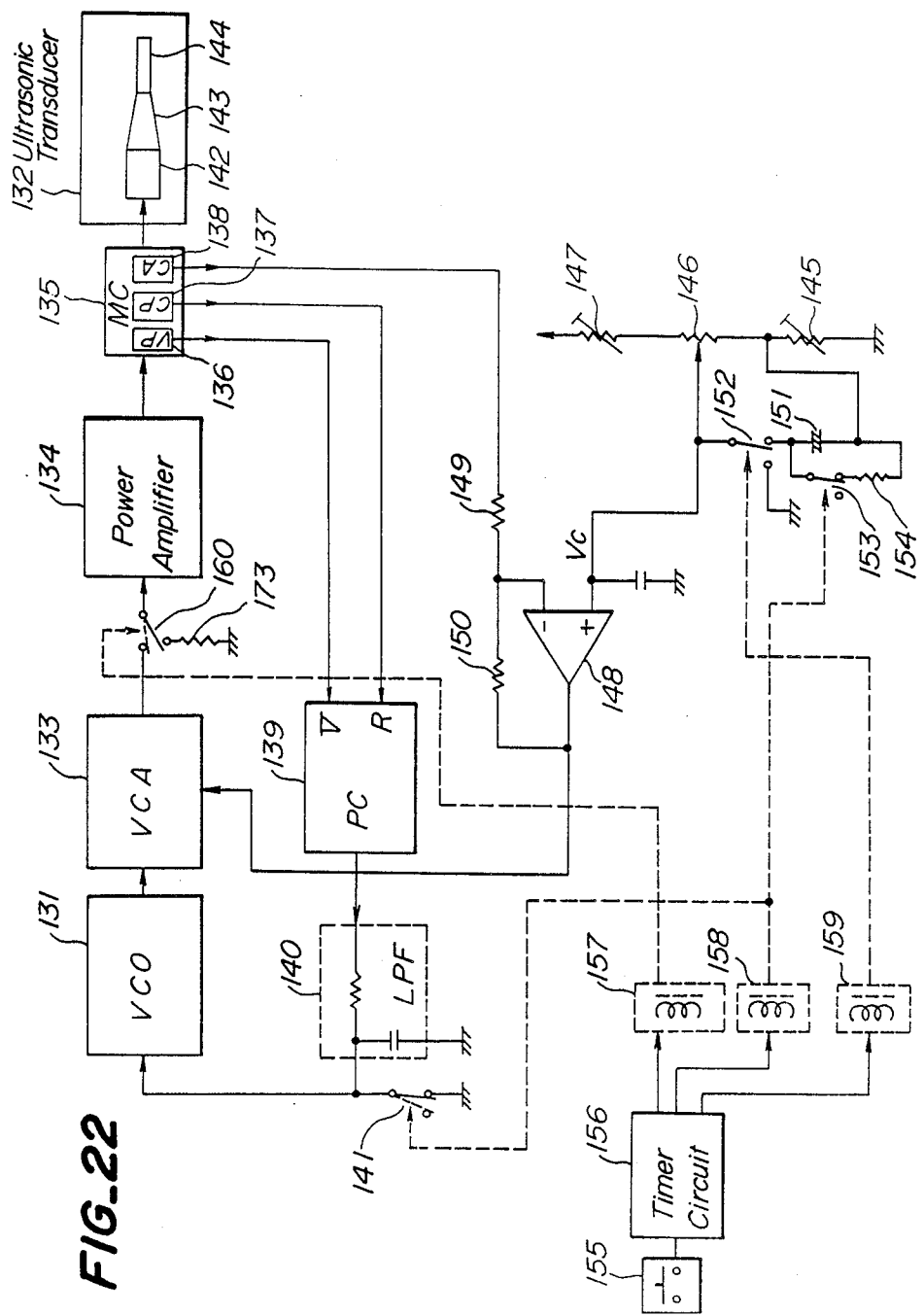
FIG._22

FIG_25

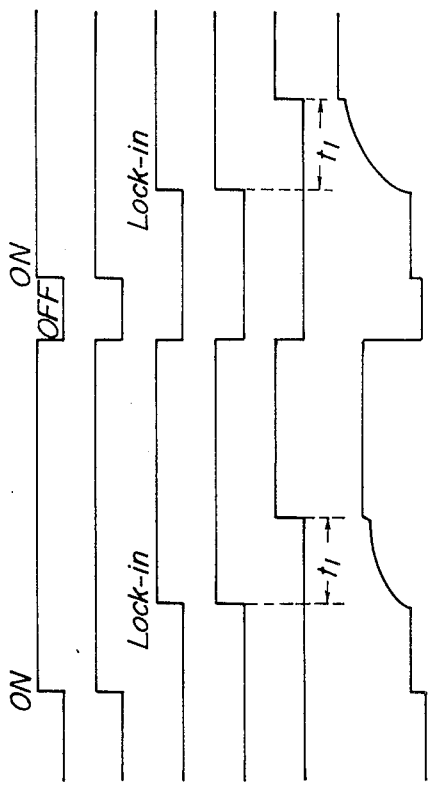
FIG.27A  Foot Switch 196
FIG.27B  Analog Switch 188
FIG.27C  Lock-in Detection
FIG.27D  Analog Switch 189
FIG.27E  Analog Switch 190
FIG.27F  Voltage Vc
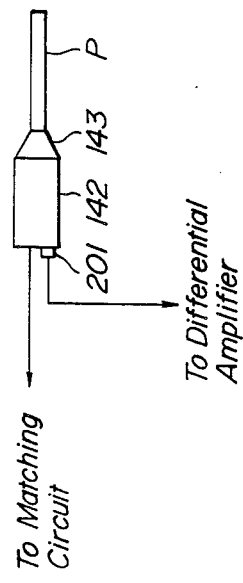
FIG.28

FIG_31
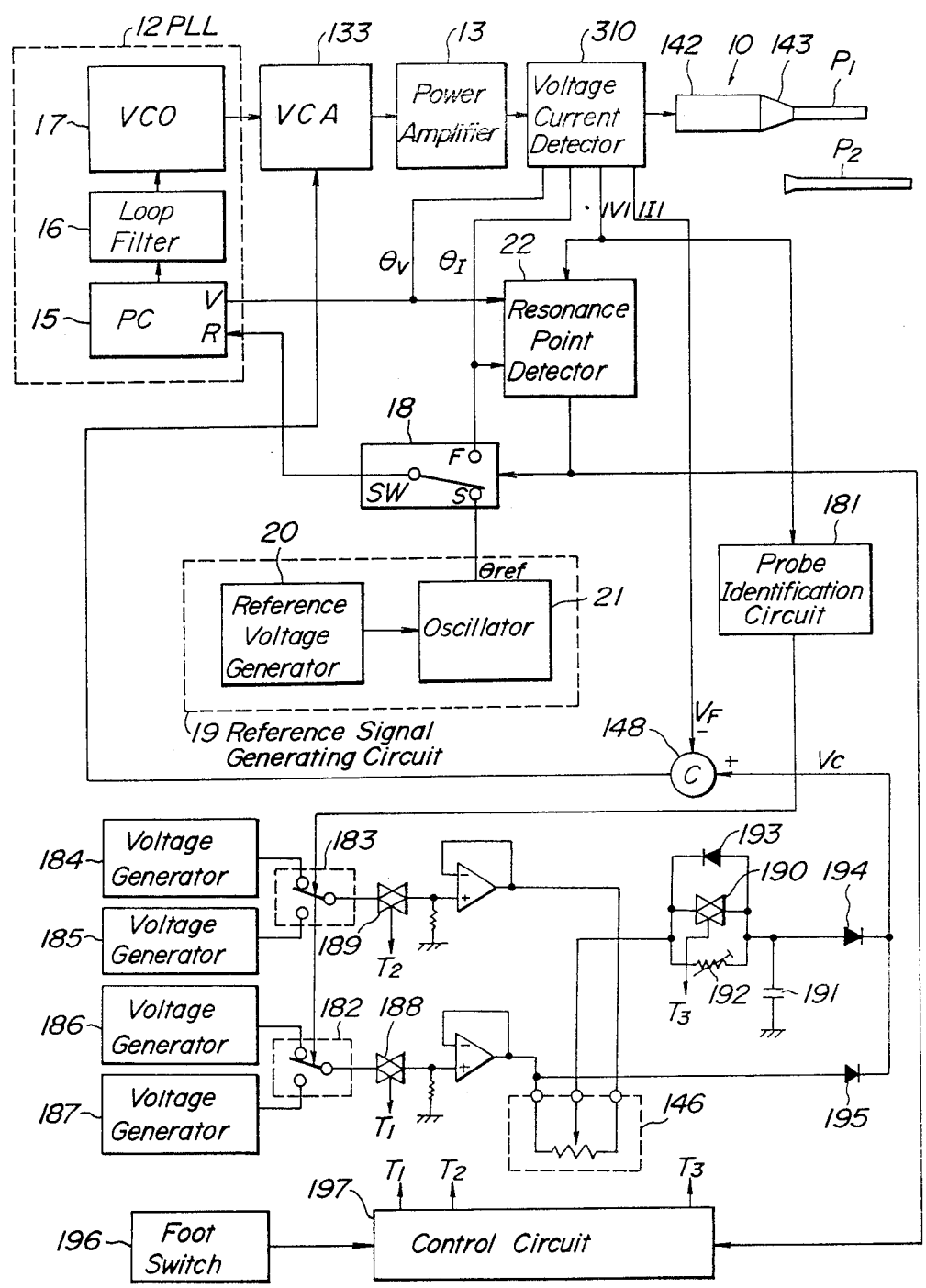

CIRCUIT FOR DRIVING ULTRASONIC TRANSDUCER

BACKGROUND OF THE INVENTION

1. Field of the Invention and Related Art Statement

The present invention relates to a circuit for driving an ultrasonic transducer, and more particularly relates to a circuit for driving an ultrasonic transducer for use in surgical operations.

There have been developed various kinds of devices using ultrasonic transducers such as ultrasonic surgical knives, ultrasonic working tools, ultrasonic atomizes, ultrasonic bonding machines and ultrasonic welding machines. In these ultrasonic devices, in order to improve the efficiency it is desired to drive the ultrasonic transducer at a resonance frequency. However, since the resonance frequency is changed in accordance with temperature variations, it is rather difficult to vibrate the ultrasonic transducer always at the resonance frequency, when there is not provided any means for compensating for the variation of the resonance frequency. Furthermore, the resonance frequency of the ultrasonic transducer is changed in accordance with the condition of the load applied thereto. Therefore, it is required to adjust or change the frequency of the driving signal in accordance with the variation of the resonance frequency of the ultrasonic transducer.

Several solutions for satisfying the above mentioned requirement have been proposed in, for instance U.S. Patent Nos. 4,275,363, 4,587,958, 4,724,401 and 4,754,186. In these known ultrasonic transducer driving circuits, there is provided a phase lock loop (PLL) and the frequency of the signal for driving the ultrasonic transducer is automatically controlled to follow the varying resonance frequency of the ultrasonic transducer. However, the inventor present has confirmed that the known ultrasonic transducer driving circuits including a PLL have a serious drawback which will be explained hereinbelow.

FIG. 1 shows an equivalent circuit of the piezoelectric type ultrasonic transducer. The ultrasonic transducer 1 is expressed by a parallel circuit of series-connected resistor R, inductor L and capacitance C and a damping capacitance $C_d$. In a practical circuit, in order to cancel the effect of the damping capacitance $C_d$, a compensating inductor $L_d$ is connected in parallel with said parallel circuit of the ultrasonic transducer 1. In such a circuit, the frequency characteristic of a phase difference $\Delta\theta$ between the driving voltage and the driving current can be represented by a curve shown in FIG. 2A, and the frequency characteristic of an impedance $|Z|$ viewed in the direction shown by an arrow A in FIG. 1 is illustrated in FIG. 2B. As illustrated in FIGS. 2A and 2B, the phase difference $\Delta\theta$ becomes zero at a resonance frequency $f_r$ as well as antiresonance frequencies $f_1$ and $f_2$, these antiresonance frequencies being positioned on respective sides of the resonance frequency $f_r$, and the impedance $|Z|$ becomes minimum at the resonance frequency $f_r$ and becomes maximum at the antiresonance frequencies $f_1$ and $f_2$. In the known driving circuit, the phase difference $\Delta\theta$ between the driving voltage and the driving current is detected to adjust the driving frequency into the resonance frequency $f_r$ through the feedback control of the PLL. As can be understood from the curves shown in FIGS. 2A and 2B, the phase difference $\Delta\theta$ becomes zero not only at the desired resonance frequency $f_r$, but also at the antiresonance frequencies $f_1$ and $f_2$, so that the feedback control of the PLL in which the frequency of the driving signal is adjusted to follow the resonance frequency of the ultrasonic transducer is effective only within the frequency range between the two antiresonance frequencies $f_1$ and $f_2$, and if the vibrating frequency of the ultrasonic transducer decreases lower than the antiresonance frequency $f_1$ or increases higher than the antiresonance frequency $f_2$, the feedback control of the PLL could not be performed correctly and the driving frequency would further decrease or increase continuously. Particularly, in the time of starting the vibration, the driving signal could not be easily locked with the vibration of the ultrasonic transducer at the desired resonance frequency $f_r$.

In order to mitigate the above mentioned drawback, it has been known to restrict the frequency control range of the PLL with the aid of a limiter. In this case, since the limiter has to be set or designed very precisely, the circuit construction is liable to be complicated, so that such a driving circuit has not been actually realized.

In the above mentioned U.S. Pat. No. 4,275,363, there has been proposed to provide a sweep circuit by means of which a control voltage applied to a control terminal of a voltage controlled oscillator (VCO) in the PLL is changed in a monotonous manner so that the oscillation frequency of the VCO is changed within a predetermined range, and when the resonance point is detected, the sweep operation is stopped and the PLL is set into the feedback control mode. However, in this known driving circuit, the output voltage from the sweep circuit is applied to the VCO at the transient between the sweep control mode and the feedback control mode and a finite voltage is applied to the VCO as an offset voltage. This offset voltage affects the loop characteristics of the PLL, and the PLL could not operate correctly.

In the U.S. Pat. No. 4,754,186, there is proposed another method of locking the oscillation frequency of the VCO to the resonance frequency of the transducer. In this known method, when the VCO oscillates at a frequency lower than the lower antiresonance frequency $f_1$, a pulse signal is added to the feedback signal in the PLL so that the oscillation frequency of the VCO is increased and is locked into the desired resonance frequency $f_r$. However, in this known method, since the locking operation is dependent upon the loop characteristics of the PLL, it is quite difficult to positively lock the oscillation frequency of the VCO into the resonance frequency $f_r$ of the ultrasonic transducer.

It should be noted that the above described problem occurs not only during the starting period but also during the usual operation. That is to say, in the case that the ultrasonic transducer is used in a surgical knife, when a very large load is applied to the ultrasonic transducer, the ultrasonic transducer could not be vibrated at the resonance frequency $f_r$ and the driving frequency might be out of the automatic resonance point following range. Then, it is necessary to effect the lock-in operation again.

SUMMARY OF THE INVENTION

The present invention has for its object to provide an ultrasonic transducer driving circuit in which the driving frequency can be positively and accurately locked into a desired resonance frequency of the ultrasonic transducer without producing any undesired offset in the phase lock loop.

According to the invention, a circuit for driving an ultrasonic transducer comprises an oscillating means for generating a driving signal whose frequency is controlled in accordance with a frequency control signal;

a first phase detecting means for detecting a phase of said driving signal to generate a first phase detection signal;

a second phase detecting means for detecting a phase of the vibration of the ultrasonic transducer to generate a second phase detection signal;

a reference signal generating means for generating a reference signal whose frequency is continuously changed; and a frequency control means for selectively changing the operation of the driving circuit between a sweep control mode in which the frequency of the driving signal generated from said oscillating means is controlled to follow the frequency of said reference signal by comparing one of said first and second phase detection signals with said reference signal and a feedback control mode in which the frequency of the driving signal generated from said oscillating means is controlled to follow a resonance frequency of the ultrasonic transducer by comparing said first and second phase detection signals with each other.

In a preferred embodiment of the driving circuit according to the invention, said first phase detecting means detects the phase of a voltage of the driving signal and said second phase detecting means detects the phase of a current of the driving signal. As is well known in the art, the ultrasonic transducer vibrates in synchronism with the driving current, so that the phase of the driving current represents the phase of the vibration of the ultrasonic transducer.

As explained above with reference to the curves shown in FIGS. 2A and 2B, the phase difference $\Delta\theta$ between the driving voltage and the driving current becomes zero and the impedance $|Z|$ of the ultrasonic transducer becomes minimum when the ultrasonic transducer vibrates at the resonance frequency $f_r$.

Therefore, in a preferred embodiment of the driving circuit according to the present invention, said frequency control means comprises a means for detecting the impedance of the ultrasonic transducer, a means for comparing the thus detected impedance with a predetermined threshold level, and a switching means for changing the operation of the driving circuit between the sweep control mode and the feedback control mode when the impedance of the ultrasonic transducer exceeds said threshold level.

As explained above, the vibration amplitude of the ultrasonic transducer is proportional to the amplitude of the driving current, so that it is preferable to energize the ultrasonic transducer under the constant current driving mode. In this case, the impedance of the ultrasonic transducer becomes proportional to the driving voltage. Therefore, in another preferred embodiment of the driving circuit according to the invention, said frequency control means comprises a means for detecting the amplitude of the voltage of the driving signal, a means for comparing the thus detected amplitude with a predetermined threshold level, and a switching means for changing the operation of the driving circuit between the sweep control mode and the feedback control mode when the amplitude of the voltage of the driving signal exceeds said threshold level.

The inventor has conducted various experiments and has found that when the driving circuit is operated under the sweep control mode, it is not necessary to keep the amplitude of the driving current at a normal value, but it is advantageous to reduce the driving current to a low safety level. According to another aspect of the invention, the amplitude of the driving current is limited to a level lower than the nominal value during the sweep control mode, and after the frequency of the driving signal is locked into the resonance frequency of the ultrasonic transducer, the amplitude of the current of the driving signal is increased to the nominal value.

The inventor has further confirmed that when the amplitude of the current of the driving signal is abruptly increased from the low value in the sweep control mode into the nominal value in the feedback control mode, the vibration frequency of the ultrasonic transducer is sometimes changed and the resonance condition might be lost. According to still another aspect of the invention, the amplitude of the current of the driving signal is increased gradually from the lower value to the nominal value for a relatively long time period when the frequency of the driving signal is locked into the resonance frequency of the ultrasonic transducer. By this measure, the frequency of the driving signal is kept at the desired resonance frequency of the ultrasonic transducer even if the amplitude of the driving current is changed from the lower value to the higher nominal value.

BRIEF DESCRIPTION OF THE DRAWINGS

FIGS. 8A to 8D are signal waveforms for explaining the operation of the driving circuit of FIG. 3;

FIG. 22 is a block diagram showing a fifth embodiment of the driving circuit according to the invention;

FIGS. 27A to 27F are signal waveforms for explaining the operation of the circuit of FIG. 26;

FIG. 28 is a schematic view showing a part of a modification of the driving circuit of FIG. 26;

FIG. 31 is a block diagram showing an eighth embodiment of the driving circuit according to the invention.

DESCRIPTION OF THE PREFERRED EMBODIMENTS

Figure 1:
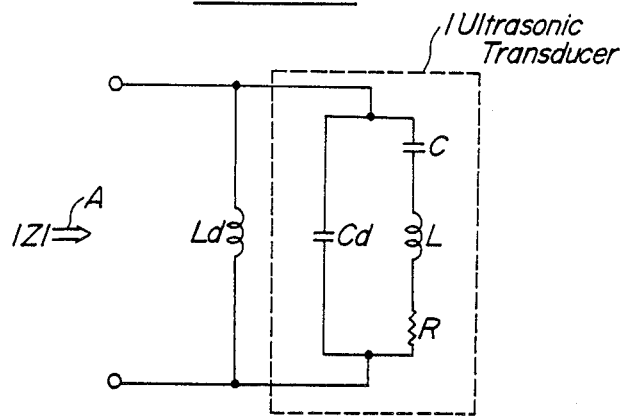
FIG. 1 is an equivalent circuit of the ultrasonic vibrating element.
Figure 2A:
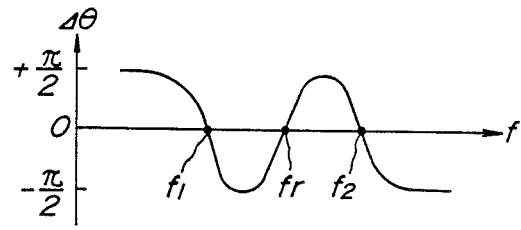
FIGS. 2A and 2B show frequency characteristics of the phase difference between the driving voltage and current and the impedance of the ultrasonic vibrating element.
Figure 2B:
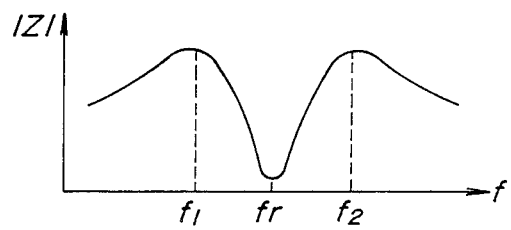
Figure 3:
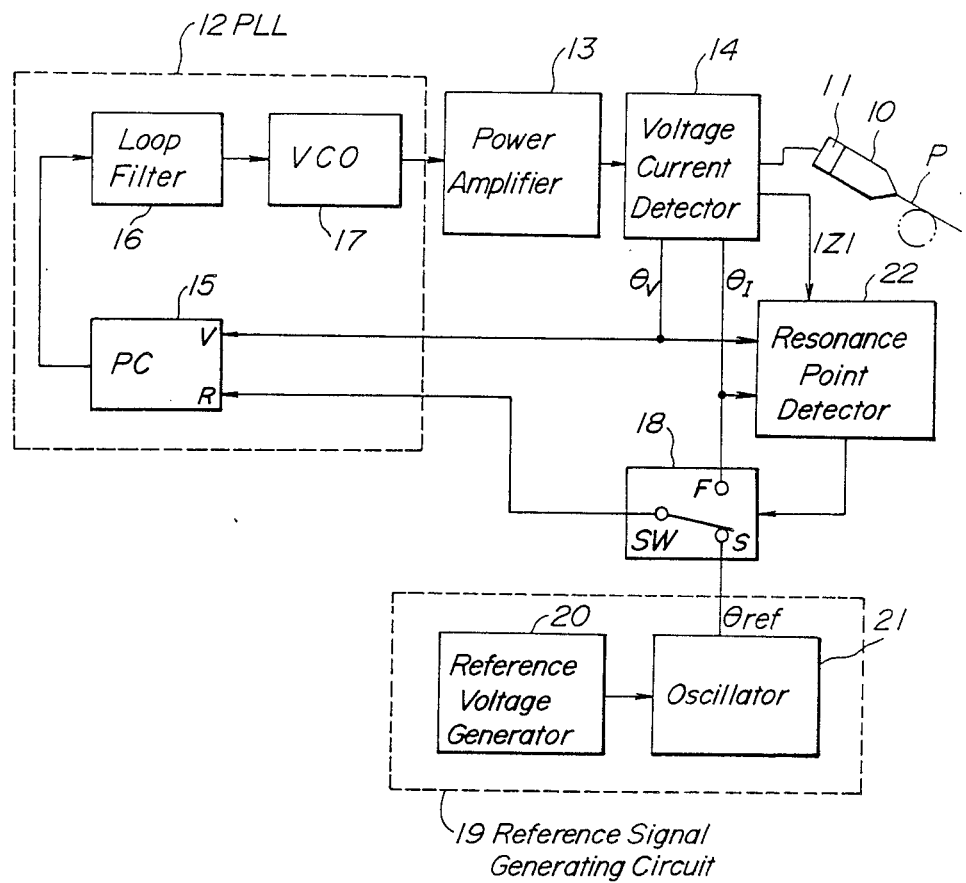
FIG. 3 is a block diagram illustrating a first embodiment of the driving circuit according to the invention.
Figure 4:
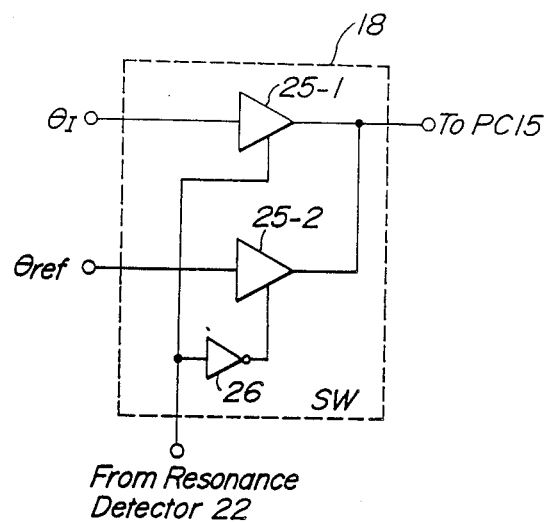
FIGS. 4, 5, 6 and 7 are circuit diagrams depicting several embodiments of the switching circuit shown in FIG. 3.

FIG. 3 is a block diagram showing a first embodiment of the ultrasonic transducer driving circuit according to the invention. In the present embodiment, the ultrasonic transducer is applied to an ultrasonic surgical knife of Langevine type. A piezoelectric ultrasonic vibrating element 11 of Langevine type is installed in a hand piece 10 and is driven by the driving circuit including a phase lock loop, i.e. PLL 12 and a power amplifier 13. Between the power amplifier 13 and the ultrasonic vibrating element 11 there is arranged a voltage-current detecting circuit 14 to detect voltage and current phases of a driving signal applied to the ultrasonic vibrating element to generate voltage phase signal $\theta_v$ and current phase signal $\theta_I$. The voltage-current detecting circuit 14 also detects an impedance of the ultrasonic vibrating element to derive an impedance signal $|Z|$. As explained above, the voltage phase signal $\theta_v$ represents the phase of the driving signal and the current phase signal $\theta_I$ expresses the vibration phase of the ultrasonic vibrating element 11. Further, the impedance $|Z|$ of the ultrasonic vibrating element 11 becomes minimum when the ultrasonic element vibrates at the desired resonance frequency $f_r$ as shown in FIG. 2A.

The phase lock loop 12 includes a phase comparator (PC) 15, a loop filter 16 and a voltage controlled oscillator (VCO) 17. An output signal from VCO 17 is supplied to the power amplifier 13 and is amplified to a level which is sufficient for driving the ultrasonic vibrating element 11. The phase comparator 15 has a variable input terminal V and a reference input terminal R, and to the variable input terminal V is applied the voltage phase signal $\theta_v$ and to the reference input terminal R is selectively supplied the current phase signal $\theta_I$ via a switching circuit (SW) 18 whose switching arm is connected to a contact F coupled with the voltage and current detecting circuit 14.

There is further provided a reference signal generating circuit 19 comprising a reference signal generator 20 and an oscillator 21 which is controlled by an output signal from the reference signal generator 20. It should be noted that the reference signal generator 20 may be formed by a voltage generator and the oscillator 21 may be constructed by the voltage controlled oscillator. A reference signal $\theta_{ref}$ generated from the reference signal generating circuit 19 is also selectively supplied to the reference input terminal R of the phase comparator 15 via the switching circuit 18. To this end, a contact S of the switching circuit 18 is connected to the reference signal generating circuit 19. The reference signal generator 20 is formed to generate a ramp voltage whose amplitude is increased monotonously, and this continuously increasing voltage is applied to the control input of the voltage controlled oscillator 21, so that the frequency of the reference signal $\theta_{ref}$ generated from the reference signal generating circuit 19 is increased also continuously.

The voltage and current phase signals $\theta_v$ and $\theta_I$ and the impedance signal $|Z|$ generated from the voltage and current detecting circuit 14 are also supplied to a resonance point detecting circuit 22. In the resonance point detecting circuit 22, whether or not the frequency of the driving signal is equal to the resonance frequency $f_r$ of the ultrasonic vibrating element 11. When the frequency of the driving signal is not identical with the resonance frequency $f_r$, the switching arm of the switching circuit 18 is connected to the contact S, and when the driving frequency becomes equal to the resonance frequency $f_r$, the switching arm is changed from the contact S to the contact F. Therefore, when the driving frequency is not equal to the resonance frequency $f_r$, the phase comparator 15 detects the phase difference between the voltage phase signal $\theta_v$ and the reference signal $\theta_{ref}$ so that the frequency of the driving signal is increased in accordance with the increasing frequency of the reference signal. When the resonance point detecting circuit 22 detects the in-phase condition, the switching arm of the switching circuit 18 is changed from the contact S to the contact F. Then, the phase lock loop 12 begins to operate normally and the frequency of the driving signal is automatically controlled to follow the resonance frequency of the ultrasonic vibrating element 11. The former operation mode is termed the sweep control mode, while the latter operation mode is called the feedback control mode.

FIGS. 4 to 7 illustrate some embodiments of the switching circuit 18 of the driving circuit according to the invention. In the switching circuit 18 shown in FIG. 4, the current phase signal $\theta_I$ and reference signal $\theta_{ref}$ are applied to three-state buffers 25-1 and 25-2, respectively. To a control terminal of the first three-state buffer 25-1 is directly applied the output signal from the resonance point detecting circuit 22 and to a control terminal of the second three-state buffer 25-2 is applied said output signal via an inverter 26. When the output signal of the resonance point detecting circuit 22 has a logic high level (H), the first three-state buffer 25-1 is made conductive and the current phase signal $\theta_I$; is applied to the reference input terminal of the phase comparator 15, and when the output signal from the resonance point detecting circuit 22 has a logic low level (L), i.e. when the frequency of the driving signal deviates from the resonance frequency of the ultrasonic vibrating element 11, the reference signal $\theta_{ref}$ is applied to the phase comparator 15 in PLL 12.

Figure 5:
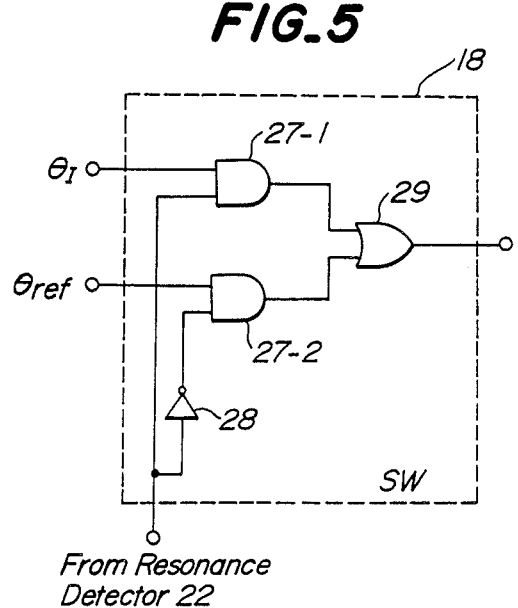

In the switching circuit 18 depicted in FIG. 5, the current phase signal $\theta_I$ and reference signal $\theta_{ref}$ are applied to one of the inputs of AND gates 27-1 and 27-2, respectively, and to the other inputs of these AND gates is applied the output signal of the resonance point detecting circuit 22 directly and via an inverter 28, respectively. When the output signal of the resonance point detecting circuit 22 has a logic high level, i.e. when the driving signal frequency is made identical with the resonance frequency of the ultrasonic vibrating element 11, the current phase signal $\theta_I$ is applied to the phase comparator 15 by means of the first AND gate 27-1, and when the output signal of the resonance point detecting circuit 22 is in the logic low level, the reference signal $\theta_{ref}$ is applied to the phase comparator via the second AND gate 27-2.

Figure 6:
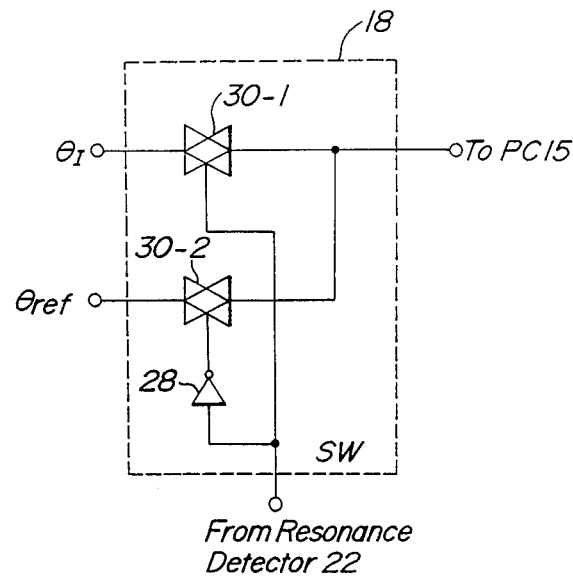

In the switching circuit 18 illustrated in FIG. 6, the current phase signal $\theta_I$ and reference signal $\theta_{ref}$ are applied to first and second analog switches 30-1 and 30-2, respectively, and the output signal of the resonance point detecting circuit 22 is applied to control terminals of these analog switches directly and via an inverter 28, respectively. Also in the present embodiment, one of the current phase signal and reference signal is selectively supplied to the phase comparator 15 in the PLL in accordance with the level of the output signal supplied from the resonance point detecting circuit 22.

Figure 7:
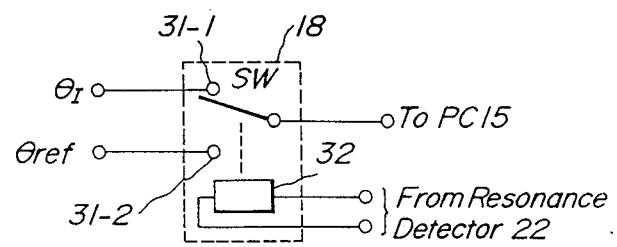

In the switching circuit 18 shown in FIG. 7, the current phase signal $\theta_I$ and reference signal $\theta_{ref}$ are applied to relay contacts 31-1 and 31-2, respectively, and the output signal of the resonance point detecting circuit 22 is supplied to a relay coil 32. When the resonance condition is detected, the relay coil 32 is energized by the output signal from the resonance point detecting circuit 22 and the current phase signal is applied to the phase comparator 15, while when the resonance point is not found, the reference signal is applied to the phase comparator.

Now the operation of the driving circuit shown in FIG. 3 will be explained in detail.

In the starting time, the switching circuit 18 is set such that the reference signal $\theta_{ref}$ is applied to the reference input terminal R of the phase comparator 15 in PLL 12 and the voltage phase signal $\theta_v$ is applied to the variable input terminal V of the phase comparator 15. Therefore, the phase comparator 15 detects a phase difference $\Delta\theta$ between these reference signal and the voltage phase signal to derive a control signal representing the detected phase difference. This control signal is supplied to the loop filter 16 having the integrating function and the frequency control voltage is generated from the loop filter and is applied to the control terminal of VCO 17 so that the frequency of the output signal of the VLO is changed to follow the monotonously varying frequency of the reference signal $\theta_{ref}$. That is to say, the frequency of the oscillation frequency Of VCO 17 becomes equal to the frequency of the reference signal $\theta_{ref}$, and therefore the frequency of the driving signal applied to the ultrasonic vibrating element 11 becomes identical with the frequency of the reference signal to effect the sweep control.

Figure 8D:
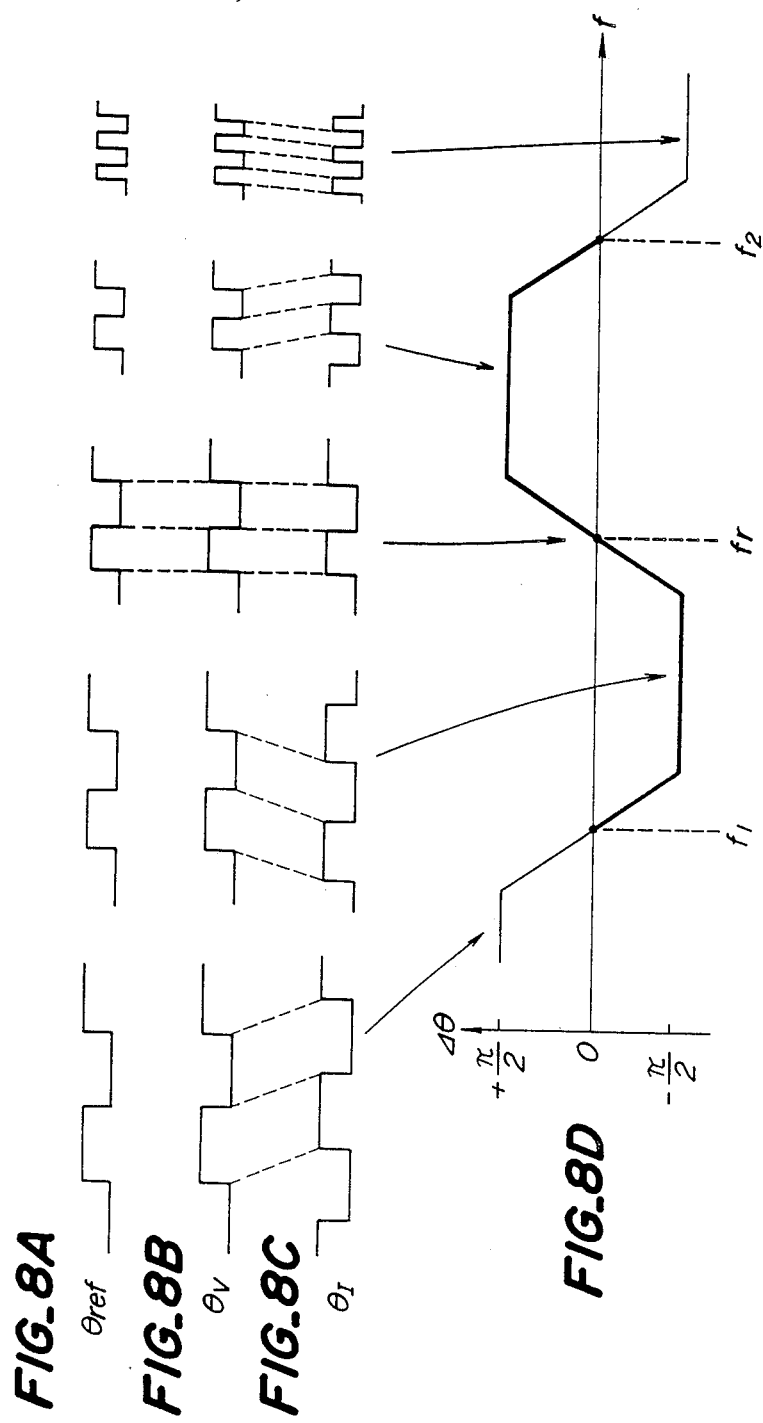

FIGS. 8A to 8D illustrate waveforms of the reference signal $\theta_{ref}$, voltage phase signal $\theta_v$, current phase signal $\theta_I$, and the phase difference $\Delta\theta$ between the current and voltage of the driving signal applied to the ultrasonic vibrating element 11. As shown in FIG. 8A, the frequency of the reference signal $\theta_{ref}$ is increased gradually. When the ultrasonic vibrating element 11 operates at the resonance frequency $f_r$, the current phase signal $\theta_I$ representing the vibration phase of the element 11 is in-phase with the voltage phase signal $\theta_v$, i.e. the phase difference $\Delta\theta$ becomes zero at the resonance frequency $f_r$. Under this condition, the phase of the current phase signal $\theta_I$ is made identical with that of the reference signal $\theta_{ref}$, because the voltage phase signal $\theta_v$ is phase-locked with the reference signal due to the function of the phase lock loop 12.

When the resonance condition is detected by the resonance point detecting circuit 22, the output signal from this circuit becomes the logic high level H and the switching circuit 18 is operated to change its switching arm from the contact S to the contact F, so that the current phase signal $\theta_I$ is applied via the switching circuit 18 to the reference input terminal R of the phase comparator 15. Then, the phase comparator 15 functions to detect the phase difference $\Delta\theta$ between the current phase signal $\theta_I$ and the voltage phase signal $\theta_v$, and the frequency of the driving signal applied to the ultrasonic vibrating element 11 is controlled such that the phase of the voltage of the driving signal is made always identical with the phase of the current of the driving signal. In other words, the frequency of the driving signal is automatically adjusted to follow the resonance frequency of the ultrasonic vibrating element 11 due to the feedback control of the PLL. According to the invention, at the time of change from the sweep control mode to the feedback control mode, the phase difference at the phase comparator 15 is maintained zero, because the voltage phase signal is locked with the reference signal and further the current phase signal is locked with the voltage phase signal. Therefore, the phase comparator 15 does not produce any offset voltage and thus the operation of the phase lock loop is not affected by the change in the control mode.

It should be noted that the detection of the resonance point in the resonance point detecting circuit 22 is carried out by monitoring the phase difference between the voltage phase signal $\theta_v$ and the current phase signal $\theta_I$ when the varying frequency of the reference signal is set within a range between the lower and higher antiresonance frequencies $f_1$ and $f_2$ shown in FIG. 8D, because in this case the phase difference becomes zero only when the frequency of the driving signal is equal to the desired resonance frequency $f_r$. However, when the ultrasonic transducer system is constructed such that various kinds of probes P may be detachably coupled with the hand piece 10, the resonance frequency of the ultrasonic vibrating element 11 may vary within a relatively wide range. In such a case, the frequency of the reference signal has to be changed over a relatively wide range accordingly. Then, the frequency of the reference signal would exceed the range between the antiresonance frequencies $f_1$ and $f_2$. In this case, the phase difference between the voltage phase signal and the current phase signal becomes zero also at the antiresonance frequencies $f_1$ and $f_2$, so that the resonance point $f_r$ could no longer be detected only by detecting the phase difference. According to one aspect of the present invention, the resonance point is detected by utilizing the fact that the impedance of the ultrasonic transducer becomes minimum at the resonance frequency $f_r$ and maximum at the antiresonance frequencies $f_1$ and $f_2$. To this end, the impedance signal $|Z|$ is also supplied to the resonance point detecting circuit 22 and is compared with a predetermined threshold level. Under the condition that the impedance of the ultrasonic transducer becomes smaller than the threshold level, the resonance point is detected as a point at which the phase difference between the voltage phase signal and the current phase signal becomes zero. Then, the phase lock loop 12 can be driven into the feedback control mode in which the frequency of the driving signal is automatically adjusted to follow the varying resonance frequency of the ultrasonic vibrating element 11 even when various kinds of ultrasonic vibrating elements and hand pieces having different resonance frequencies are used.

Figure 9:
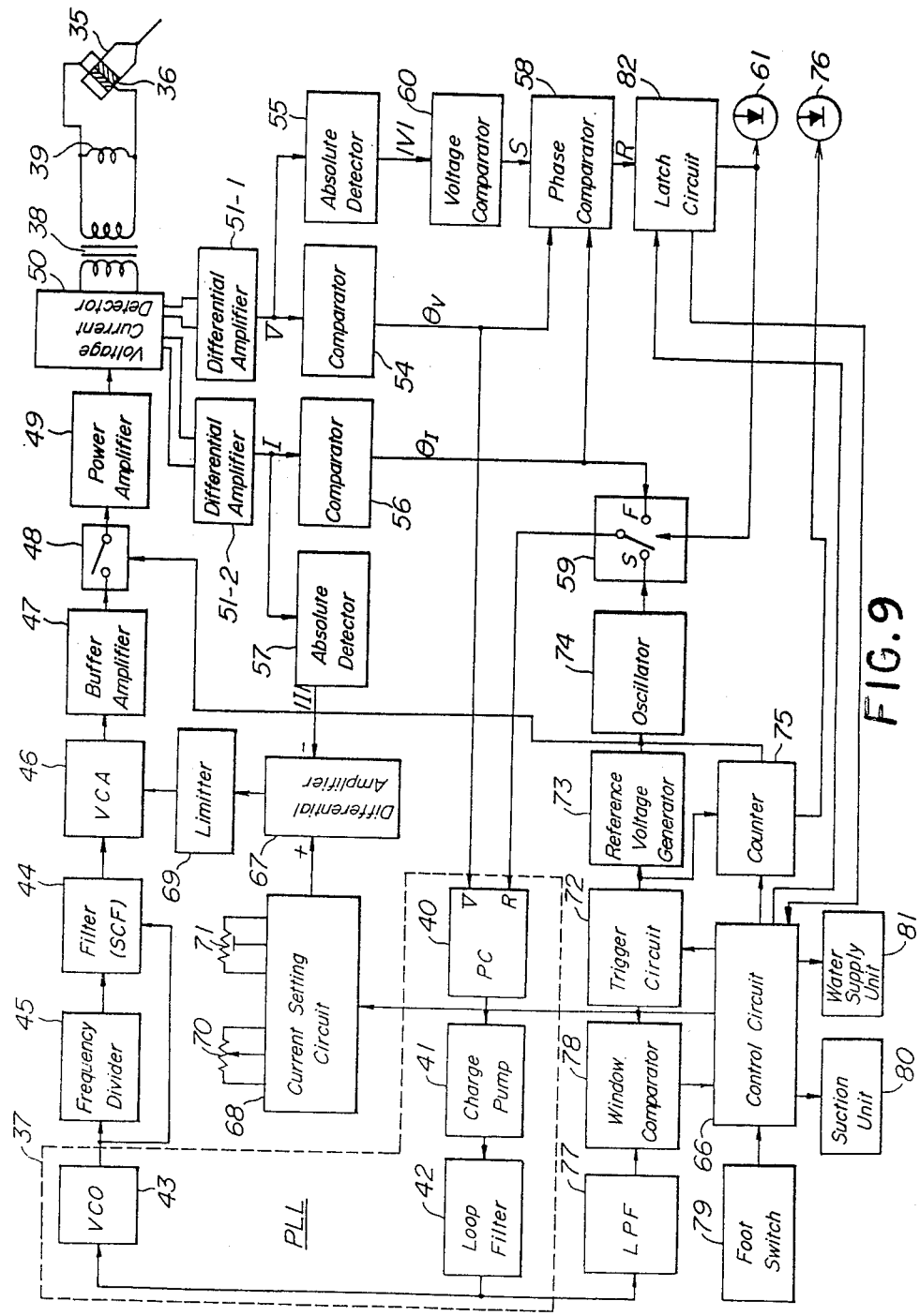
FIG. 9 is a block diagram illustrating a second embodiment of the driving circuit according to the invention.

FIG. 9 is a block diagram showing an embodiment of an ultrasonic surgical knife comprising the driving circuit according to the present invention. An ultrasonic vibrating element 36 of Langevine type provided in a hand piece 35 is driven by an output signal derived from a phase lock loop 37 via a matching transformer 38. The ultrasonic vibrating element 36 is connected to a secondary side of the matching transformer 38. In the secondary side of the matching transformer 38, there is also connected a correcting inductor 39 for canceling the damping capacitance of the vibrating element 36.

The phase lock loop 37 comprises phase comparator (PC) 40, charge pump 41 for converting a digital output signal from the phase comparator into an analog signal, loop filter 42 and voltage controlled oscillator (VCO) 43. The analog signal generated from the charge pump 41 is supplied to the loop filter 42 having the integrating function and the control voltage generated from the loop filter is applied to VCO 43, so that the frequency of the oscillation signal generated from the VCO is changed in accordance with the control voltage. This output signal of VCO 43 is supplied to a frequency divider 45 as well as a filter 44 and an output signal of the frequency divider is also supplied to the filter 44, so that the rectangular output signal generated from VCO 43 is converted into a sinusoidal driving signal having only the resonance frequency component of the ultrasonic vibrating element 36. This contributes to minimizing the heat generation wasted in the ultrasonic vibrating element.

In the present embodiment, the filter 44 is formed by a switched capacitor filter (SCF) whose cutoff frequency can be changed by an external clock input. Then, the variation in magnitude and phase rotation of the output signal from the filter can be removed even if the oscillation frequency of VCO 43 is changed, and therefore it is possible to effect an ideal conversion from a rectangular signal into a sinusoidal signal and the phase lock loop and the constant current operation are substantially unaffected.

The output signal from the filter 44 is supplied to the primary side of the matching transformer 38 by means of voltage controlled amplifier (VCA) 46 whose amplification factor can be controlled by a control voltage, buffer amplifier 47, switching circuit 48 and power amplifier 49. The matching transformer 38 functions to isolate electrically the driving circuit from the ultrasonic transducer circuit and to take the matching between the power amplifier 49 and the load including the ultrasonic vibrating element 36.

The voltage applied to the ultrasonic vibrating element 36 via the power amplifier 49 and the current passing through the ultrasonic element are detected by a voltage and current detecting circuit 50 connected in the primary side of the matching transformer 38. Voltage detection signal and current detecting signal from the circuit 50 are supplied to differential amplifiers 51-1 and 51-2, respectively to remove in-phase noise contained therein.

Figure 10:
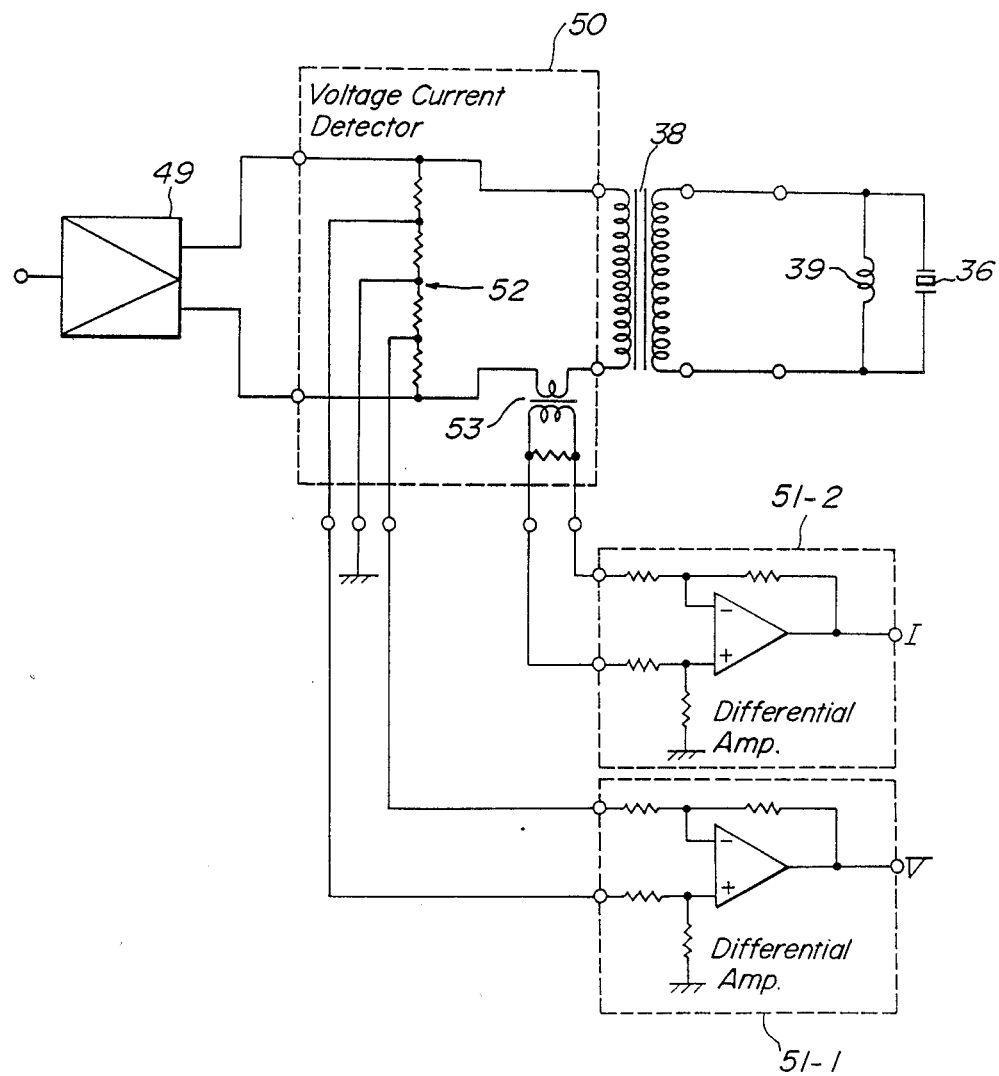
FIG. 10 is a circuit diagram showing the detailed construction of the voltage-current detector shown in FIG. 9.

FIG. 10 shows a detailed circuit of the voltage and current detecting circuit 50 and the differential amplifiers 51-1 and 51-2. The voltage to be applied to the ultrasonic vibrating element 36 is detected with the aid of a potentiometer 52 and the detected voltage is applied to the differential amplifier 51-1 to obtain the voltage detection signal V. The current passing through the ultrasonic vibrating element 36 is detected by a current transformer 53 and the detected signal is applied to the differential amplifier 51-2 to derive the current detection signal I. By detecting the high driving voltage and large driving current with the aid of the differential amplifiers 51-1 and 51-2, the problem of the in-phase noise can be effectively solved and further the voltage and current detection signals V and I can be obtained stably even if the positive and negative output terminals of the power amplifier 49 are interchanged or one of the output terminals is not connected to the ground potential.

As shown in FIG. 9, the voltage detection signal V is supplied to a comparator 54 and an absolute value detector 55. In the comparator 54, the phase i.e. polarity of the voltage signal V is detected to derive the voltage phase signal $\theta_v$, and the absolute value $|V|$ of the amplitude of the voltage detection signal V is detected by the absolute value detector 55. In a similar manner, the current detection signal I is supplied to differential amplifier 56 and an absolute value detector 57 to derive the current phase signal $\theta_I$ and an absolute value $|I|$ of the current detection signal.

Figure 11:
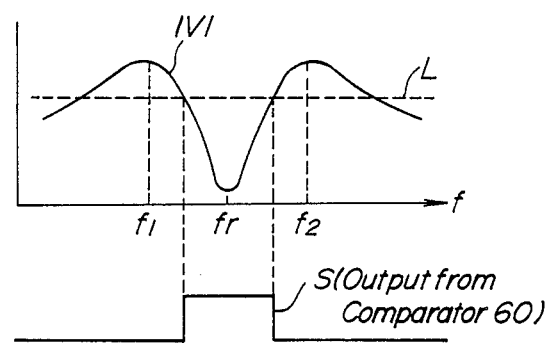
FIG. 11 shows the frequency characteristic of the driving voltage.

The voltage phase signal $\theta_v$ derived from the comparator 54 is supplied to a phase comparator 58 as well as a variable input terminal V of the phase comparator 40 of PLL 37. The current phase signal $\theta_I$ derived from the comparator 56 is supplied to the phase comparator 58 as well as to a contact F of a switching circuit 59. The absolute voltage signal $|V|$ derived from the absolute value detector 55 is supplied to a voltage comparator 60. The frequency characteristic of the absolute value of the voltage detection signal is shown in FIG. 11. In the voltage comparator 60, the absolute voltage value $|V|$ is compared with a predetermined threshold value L, and the voltage comparator produces an output signal S when the absolute value is decreased so as to be smaller than the threshold value L. Since the driving circuit of the present embodiment operates in the constant current mode, the absolute value of the driving voltage represents the impedance of the ultrasonic vibrating element 36. When the voltage comparator 60 generates the signal S, the phase comparator 58 is enabled to detect the phase difference $\Delta\theta$ between the voltage phase signal $\theta_v$ and the current phase signal $\theta_I$. When the frequency of the driving signal becomes equal to the desired resonance frequency $f_r$ of the ultrasonic vibrating element 36, the phase difference $\Delta\theta$ becomes zero as illustrated in FIG. 2A. Then, the phase comparator 58 generates a resonance detection signal R. This resonance detection signal R is supplied to a latch circuit 82 to change the state of the latch circuit 82. Then, the switching arm of the switching circuit 59 is changed from the contact S to the contact F and the current phase signal $\theta_I$ is supplied to the reference input terminal R of the phase comparator 40 and PLL 37 is operated in the feedback control mode in which the driving signal frequency is automatically controlled to follow the resonance frequency of the ultrasonic vibrating element 36. At the same time, a light emitting diode 61 is lit to denote that PLL 37 is driven into the feedback control mode. It should be noted that the output signal derived from the latch circuit 82 is also supplied to a control circuit 66. The function of this control circuit 66 will be explained in detail hereinafter.

Figure 12:
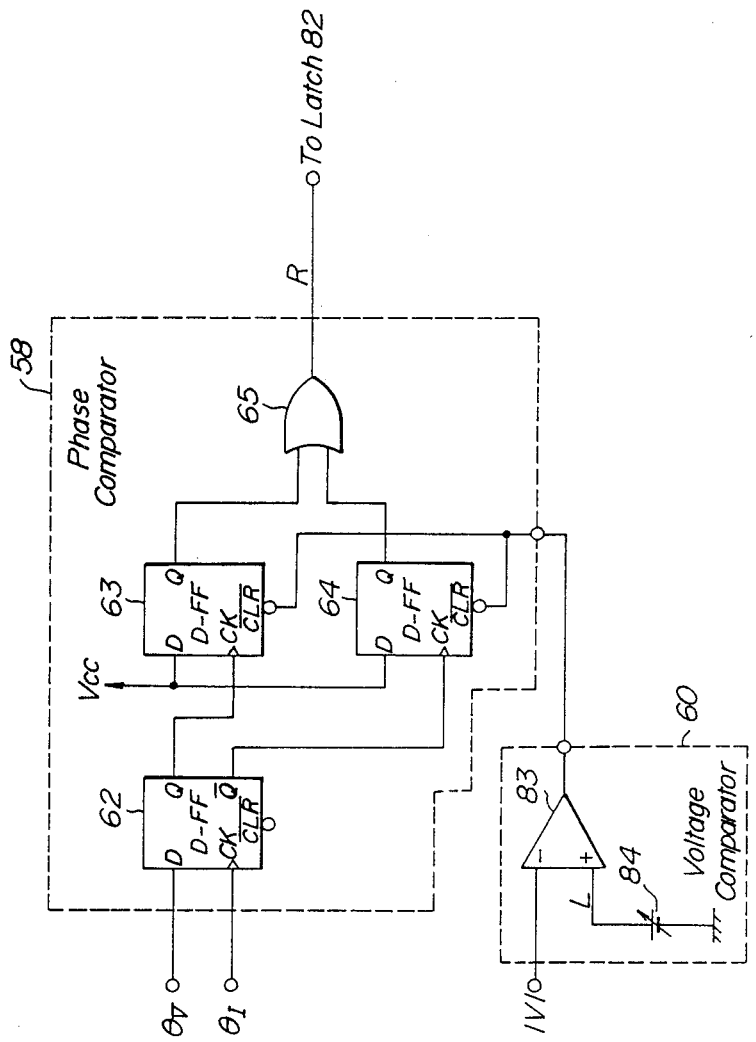
FIG. 12 is a circuit diagram showing the phase comparator shown in FIG. 9.

FIG. 12 is a circuit diagram illustrating a detailed construction of the phase comparator 58 and voltage comparator 60. The phase comparator 58 includes three D-flip-flops (D-FF) 62, 63, 64 and an OR gate 65. The voltage phase signal $\theta_v$ generated from the phase comparator 54 is applied to D-input of the first D-FF 62 and the current phase signal $\theta_I$ generated from the phase comparator 56 is applied to clock input CK of D-FF 62. Q and $\overline{Q}$ outputs of this D-FF 62 are applied to clock input CK of D-FF 63 and clock input CK of D-FF 64, and Q outputs of these D-FFs 63 and 64 are applied to the OR gate 65. An output signal from the OR gage 65 is supplied to the latch circuit 82 as the resonance point detection signal R. To D inputs of D-FFs 63 and 64 are applied a supply source voltage $V_{cc}$. The voltage comparator 60 comprises an operational amplifier 83 and the absolute voltage signal $|V|$ derived from the absolute value detector 55 is applied to an inverted input of the operational amplifier and a variable voltage source 84 is connected to the non-inverted input. A voltage set by the variable voltage source 84 represents the threshold level L shown in FIG. 11. An output signal from the operational amplifier 83 is applied to clear terminals of D-FFs 63 and 64.

As illustrated in FIG. 9, the absolute current signal $|I|$ generated from the absolute value detector 57 is supplied to an inverted input of a differential amplifier 67. To a non-inverted input of the differential amplifier 67 is applied a preset signal generated from a current setting circuit 68. An output signal of the differential amplifier 67 is applied, via a limiter 69, to the voltage controlled amplifier 46 to control the amplification factor thereof such that the ultrasonic vibrating element 36 is always driven by the predetermined current which is set by the current setting circuit 68. To the current setting circuit 68 are connected a first variable resistor 70 for setting a higher driving current level and a second variable resistor 71 for adjusting a lower driving current level. The current setting circuit 68 is controlled by a control signal supplied from the control circuit 66 such that during the starting time period, the driving current is set to the lower current level and after the PLL has been driven into the feedback control mode, the driving current is increased into the higher current level. In the manner explained above, the absolute current value $|I|$ is compared with the preset voltage supplied from the current setting circuit 68 in the differential amplifier 67 and the amplification factor of VCA 46 is controlled by the difference therebetween to control the driving signal to be applied to the buffer amplifier 47 and power amplifier 49. Therefore, even when the impedance is varied due to the variation in the load to the hand piece 35, it is possible to drive the ultrasonic vibrating element 36 with the constant current having the value set by the current setting circuit 68, so that the vibration amplitude of the hand piece 35 can be maintained constant.

To the control circuit 66 is connected a trigger circuit 72 to generate a trigger signal under the control of the control circuit. The trigger signal is applied to a reference voltage generator 73 to generate a reference voltage signal having a sawtooth waveform. This sawtooth voltage signal is applied to an oscillator 74 formed by the voltage controlled oscillator to generate the reference signal $\theta_{ref}$ having the monotonously increasing frequency. The frequency range of the oscillator 74 is substantially identical with that of VCO 43 in PLL 37.

Figure 13:
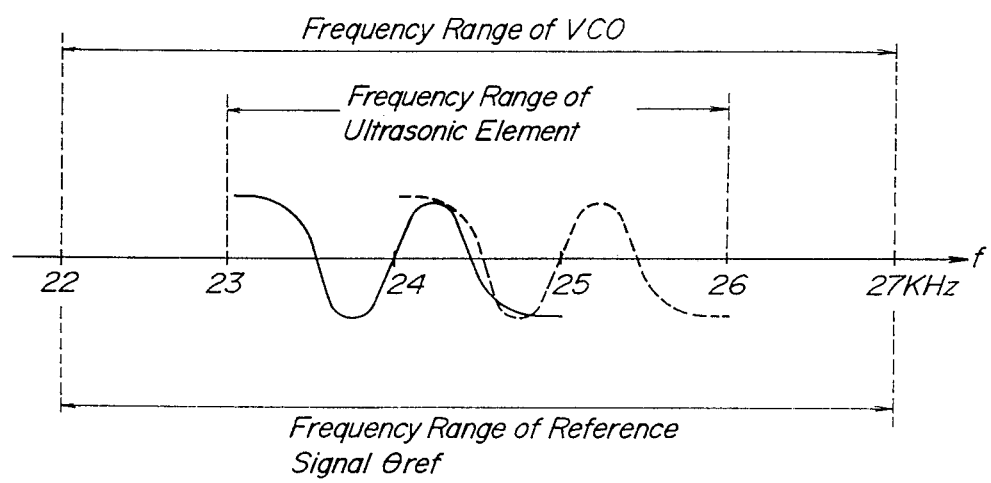
FIG. 13 is a diagram representing the frequency ranges of the voltage controlled oscillator and ultrasonic transducers.

FIG. 13 is a schematic view showing an example of the frequency ranges of the oscillator 74 and VCO 43. As shown in FIG. 13, the oscillator 74 and VCO 43 generate the signals whose frequency is varied from 22 KHz to 27 KHz. In FIG. 13 there are also illustrated the frequency characteristics of two ultrasonic vibrating elements. It should be noted that these ultrasonic vibrating elements are designed to operate within a frequency range from 23 KHz to 26 KHz. In the starting period, the control circuit 66 sends a signal to the latch circuit 82 to reset it, and the switching circuit 59 is set by the latch circuit such that its switching arm is connected to the contact S. Therefore, the reference signal $\theta_{ref}$ is supplied to the reference input terminal R of the phase comparator 40 in PLL 37. The trigger signal generated by the trigger circuit 72 is also supplied to a counter 75 which counts the number of the trigger signals generated from the trigger circuit 72. When the counter 75 has counted a predetermined number of trigger signals, it produces an abnormal detection signal by means of which the switching circuit 48 is opened and a light emitting diode 76 is lit to indicate that any abnormal condition has occurred. It should be noted that the counter 75 is reset by a signal supplied from the control circuit 66 when PLL 37 is changed from the sweep control mode to the feedback control mode.

The output signal from the loop filter 42 in PLL 37 is also supplied to a low pass filter (LPF) 77 to remove spike noise contained in the control voltage for VCO 43. The output of the low pass filter 77 is applied to a window comparator 78. In the window comparator 78, the control voltage for VCO 43 is compared with lower and upper threshold levels, these threshold levels corresponding to the lower and upper frequencies of the frequency range of the voltage controlled oscillator 43 as well as the oscillator 74. That is to say, in the present embodiment, the lower threshold level of the window comparator 78 corresponds to 23 KHz and the upper threshold level corresponds to 26 KHz as can be understood from the drawing of FIG. 13. When the control voltage becomes lower or higher than the lower or upper threshold levels, the window comparator 78 sends a reset signal to the control circuit 66. Then, the control circuit 66 sends a reset signal to the trigger circuit 72 to generate the trigger signal, and at the same time, the control circuit 66 sends a reset signal to the latch circuit 82 to reset its condition. Therefore, the reference signal $\theta_{ref}$ is generated from the oscillator 74 and the switching circuit 59 is driven to selectively supply the reference signal to the phase comparator 40 in PLL 37. If the above explained resetting means is not provided, the oscillation frequency of VCO 43 is decreased or increased up to the lowest or highest frequency when the frequency of the driving signal becomes out of the automatic resonance frequency following range. In the present embodiment, the out-of lock condition is detected by the window comparator 78 and as soon as the driving frequency is at a point out of the frequency range of the ultrasonic vibrating element 36, PLL 37 is changed into the sweep control mode. The control voltage applied to the control terminal of VCO 43 is smoothed to a certain extent by the loop filter 42, but when use is made of the edge trigger type phase comparator 40 and the loop filter must be designed to have a relatively high speed characteristic, so that the control voltage to be applied to VCO 43 might contain spike noise at edges of the two input signals to the phase comparator 40. This spike noise might affect the operation of the window comparator 78. In the present embodiment, such spike noise can be removed by the low pass filter 77.

To the control circuit 66 there are further connected a foot switch 79, a suction unit 80 for sucking body tissues cut by the ultrasonic surgical knife, and a water supply unit 82 for cooling the probe P coupled with the hand piece 35 as well as for washing the cut portion of the body.

Figure 14:
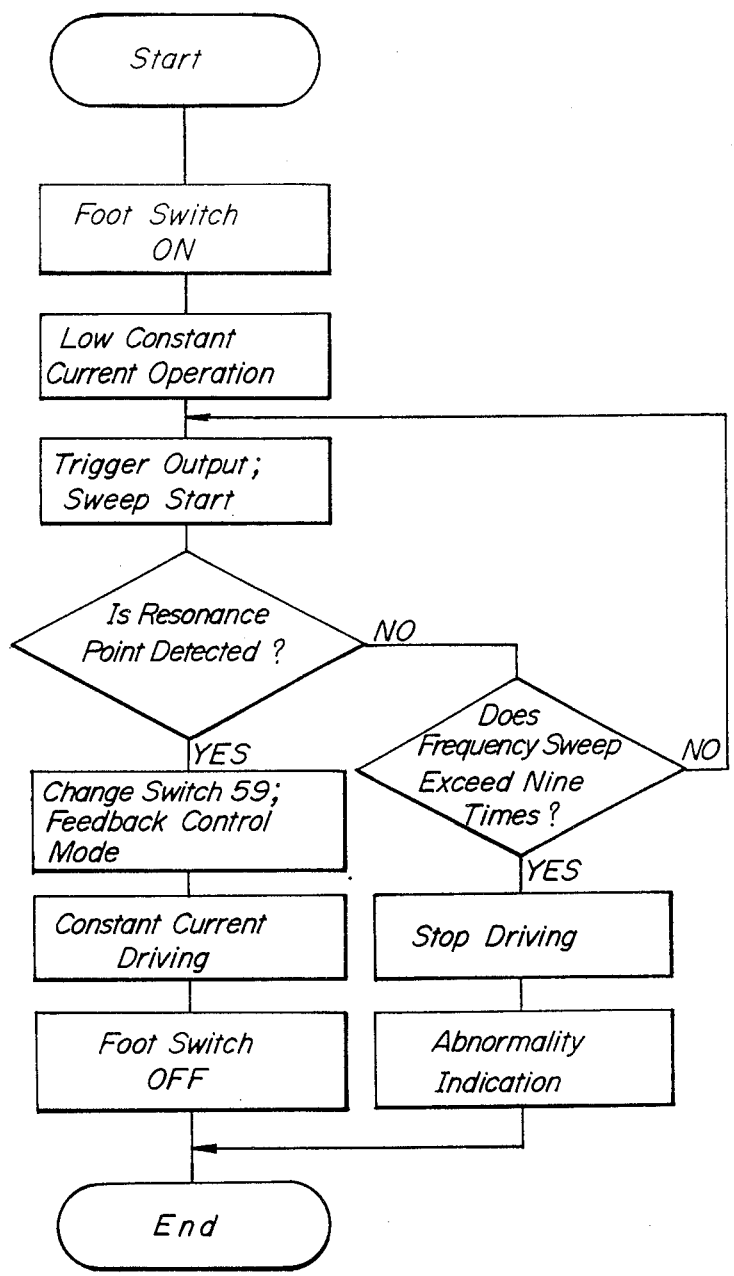
FIG. 14 is a flow chart showing the operation of the driving circuit illustrated in FIG. 9.

Now the operation of the ultrasonic surgical knife according to the present embodiment will be explained in detail also with reference to a flow chart shown in FIG. 14.

As long as the foot switch 79 is in the off position, the switch 48 is opened and the switching circuit 59 is driven such that the switching arm is connected to the contact S so that the reference signal generated from the oscillator 74 will be supplied to the reference input terminal R of the phase comparator 40.

When the operator pushes down the foot switch 79 with his or her foot to enter the start signal to the control circuit 66, the control circuit resets the latch circuit 82 and counter 75 and sends the selection signal to the current setting circuit 68 to select the lower constant current setting variable resistor 71, so that the current setting circuit applies the lower current setting voltage to the differential amplifier 67. At the same time, the control circuit 66 sends the control signal to the switch 48 so that the switch is closed. Furthermore, the control circuit 66 supplies the reset signal to the trigger circuit 72 to generate the trigger signal. Then, the reference voltage generator 73 starts to generate the sawtooth shape reference voltage and the oscillator 74 starts to generate the reference signal $\theta_{ref}$ having a frequency which is increased linearly. This reference signal $\theta_{ref}$ is supplied to the reference input terminal R of the phase comparator 40 by means of the switching circuit 59. At the same time, the voltage phase signal $\theta_v$ generated from the comparator 54 is applied to the variable input terminal V of the phase comparator 40. After the phase lock loop 37 has been driven into the phase lock condition, it operates to sweep the driving frequency in accordance with the linearly varying frequency of the reference Signal $\theta_{ref}$.

As explained above, in the sweep control mode, the current setting circuit 68 operates to generate the lower current setting voltage, so that the current amplitude current of the driving signal is maintained at the predetermined lower level. The impedance of ultrasonic vibrating element 36 is proportional to the voltage of the driving signal, because the ultrasonic element is driven under the constant current mode. The variation of the driving signal voltage is detected by the voltage-current detecting circuit 50, differential amplifier 51-1 and absolute value detector 55 and is monitored in the voltage comparator 60 and is compared with the predetermined threshold level L. When the absolute value of the driving voltage $|V|$ becomes smaller than the threshold level, i.e. the impedance of the ultrasonic vibrating element 36 is reduced so as to be lower than the predetermined value, the enabling signal S is supplied to the phase comparator 58 and the phase comparator is allowed to compare the phases of the voltage and current phase signals $\theta_v$ and $\theta_I$ with each other. When the driving signal becomes in-phase with the resonance vibration of the ultrasonic vibrating element 36, the phase difference between these signals becomes zero and the phase comparator 58 generates the resonance point detection signal R. Then, the latch circuit 82 is set by this signal R and the output signal of the latch circuit 82 is supplied to the switching circuit 59 to change the switching arm from the contact S to the contact F, so that PLL 37 is driven to operate in the feedback control mode. At the same time, the light emitting diode 61 is lit by the output of the latch circuit 82. The latch circuit 82 also sends, to control circuit 66, the signal which represents that the driving frequency has been locked with the desired resonance frequency $f_r$ of the ultrasonic vibrating element 36. In response to this, the current setting circuit 68 is controlled to select the higher current setting variable resistor 70 and the higher current level setting voltage is applied to the differential amplifier 67, so that the current of the driving signal is adjusted to the predetermined higher level. Since PLL 37 operates in the feedback control mode, the frequency of the driving signal is automatically adjusted to the resonance frequency $f_r$ of the ultrasonic vibrating element 36. When PLL 37 is driven into the feedback control mode, the control circuit 66 supplies the control signals to the suction unit 80 and water supply unit 81 and the desired operation is performed. Since this operation has been known in the relevant art detailed explanation thereof is omitted herein. The above operation is continued until the foot switch 79 is made off.

If the resonance point is not found during the single frequency sweep, the frequency of the output oscillation of VCO 43 will be increased up to the maximum frequency of 27 KHz of the frequency range of VCO 43 and oscillator 74. In the present embodiment, the frequency control voltage produced from the loop filter 42 in PLL 37 is monitored by the window comparator 78, and when this voltage becomes higher than the upper threshold value corresponding to the maximum frequency of 26 KHz of the frequency range of the ultrasonic vibrating element 36, the window comparator 78 supplies the reset signal to the control circuit 66, so that the trigger circuit 72 is driven again. Then, the oscillator 74 restarts the generation of the reference signal $\theta_{ref}$ having the varying frequency to effect the frequency sweep again. In this manner, the frequency sweep operation is repeated until the driving signal is locked with the resonance frequency of the ultrasonic vibrating element. The number of the reset operations is counted by the counter 75, and if the count value reaches a predetermined value such as ten, the switch 48 is forced to be in the off mode and the light emitting diode 76 is lit to indicate that the driving signal could not be locked with the resonance frequency of the ultrasonic vibrating element 36. Then, the operator can know that an abnormal condition has occurred in the hand piece 35. In this manner, it is possible to avoid any danger which might be produced when the ultrasonic vibrating element is continued to be driven under the abnormal condition.

Figure 15:
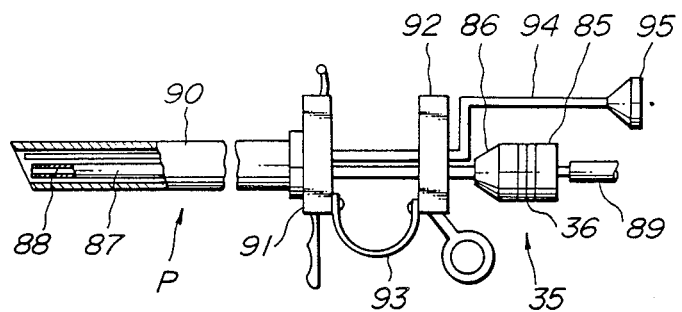
FIG. 15 is a side view depicting the ultrasonic transducer and the probe connected thereto.

FIG. 15 is a side view showing the detailed construction of the hand piece 35 and the probe P coupled thereto. The ultrasonic vibrating element 36 is secured to a main body 85 of the hand piece 35. To the main body 85 is secured a hone 86 for amplifying the vibration of the ultrasonic vibrating element and a flexible tube 87 is connected to the hone. Within the tube 87, there is formed a conduit 88 which is in communication with a suction tube 89 via the hand piece 35. The tube 87 is installed in a flexible insertion tube 90 of the endoscope. At the proximal end of the insertion tube 90 are provided a handle section 91 and a slider 92, and the tube 87 is secured to the slider 92. The slider 92 is biased by a spring 93 to move away from the handle section 91. By moving the slider 92 toward the handle section 91 against the force of the spring 93, the distal end of the tube 87 is caused to protrude from the tip of the insertion tube 90 and is brought into rough contact with the tissues of body to be processed. Within the tube 90, there is also arranged an optical observing device 94 including light guide optical fiber bundle, image guide optical fiber bundle, and an eye piece 95 coupled with the image guide fiber bundle is provided at the proximal end of the optical observing device 94.

Figure 16:
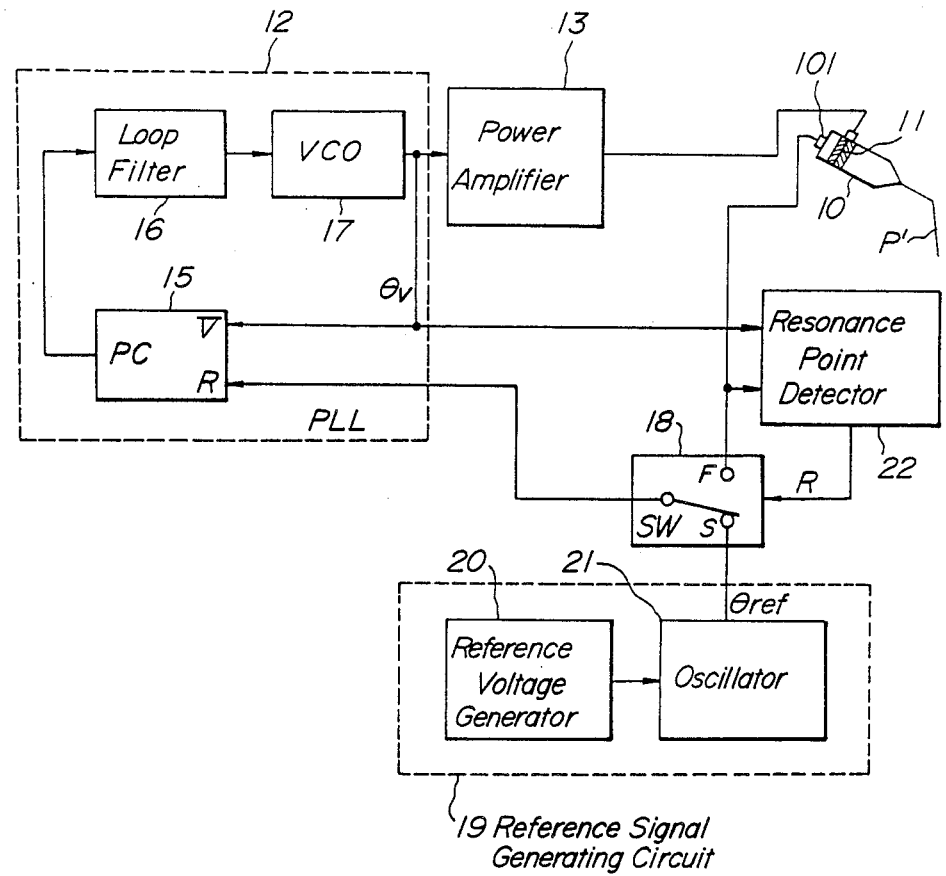
FIG. 16 is a block diagram illustrating a modification of the first embodiment of the driving circuit according to the invention shown in FIG. 3.

FIG. 16 is a block diagram showing a modification of the embodiment illustrated in FIG. 3. In this modified embodiment, portions similar to those shown in FIG. 3 are denoted by the same reference numerals used in FIG. 3 and their explanation is omitted. As depicted in FIG. 16, to the hand piece 10 is secured a vibration pick-up sensor 101 for directly detecting the vibration phase of the ultrasonic vibrating element 11, and the output signal of the vibration pick-up sensor is supplied to the resonance point detecting circuit 22 to which is also supplied the voltage phase signal $\theta_v$. In the resonance point detecting circuit 22, the vibration phase of the ultrasonic element 11 is compared with the phase of the driving voltage and when they are inphase, there is produced the resonance point detection signal R. Further, in the present embodiment, a short curved probe P' is coupled with the hand piece 10.

Figure 17A:
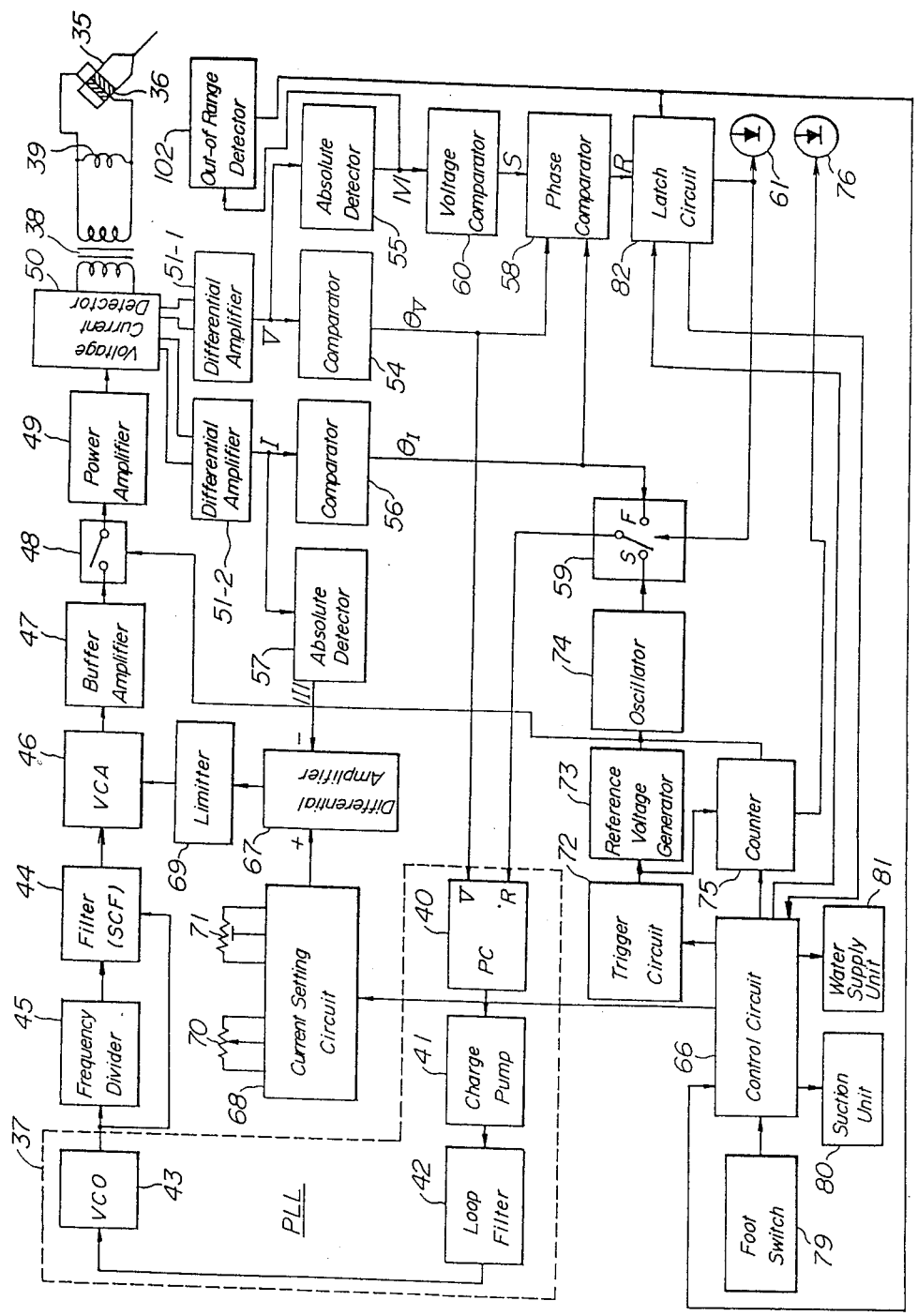
FIG. 17A is a block diagram showing a modification of the second embodiment of the driving circuit according to the invention illustrated in FIG. 9.

FIG. 17A is a block diagram illustrating a modification of the embodiment shown in FIG. 9 and portions similar to those shown in FIG. 9 are represented by the same reference numerals used in FIG. 9. In the embodiment of FIG. 9, the frequency control voltage in PLL 37 is compared with the lower and upper threshold levels in the window comparator 78 to detect the situation in which the driving frequency is changed beyond the frequency range of the oscillator 74 and VCO 43. In the present embodiment, this judgment is carried out by monitoring the variation of the voltage of the driving signal. To this end, the absolute voltage value $|V|$ is applied to an out-of range detecting circuit 102 having the differential function.

Figure 17B:
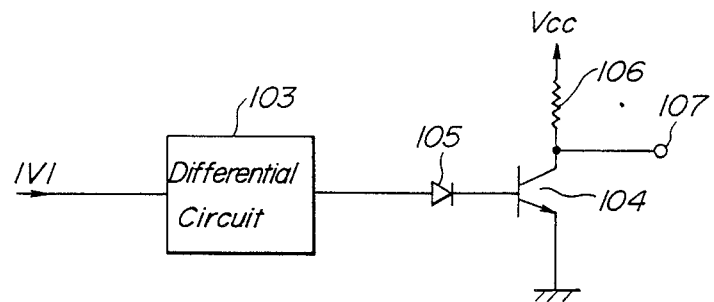
FIG. 17B is a circuit diagram showing the detailed construction of the in-phase detector shown in FIG. 17A.

FIG. 17B is a circuit diagram showing the detailed construction of the out-of range detecting circuit 102. The absolute value of the driving voltage $|V|$ is first applied to a differentiating circuit 103 and an output of the differentiating circuit is applied to a base of a switching transistor 104 via a diode 105. The collector of the transistor 104 is connected to a voltage supply source $V_{cc}$ by means of a resistor 106 and a junction point between the collector and the resistor 106 is connected to an output terminal 107. When the phase of the driving voltage becomes out-of the vibration phase of the ultrasonic vibrating element to such an extent that the phase-lock is not obtained, the differentiating circuit 103 produces a large differentiating output, and thus the base potential of the transistor 104 is increased and the transistor is made conductive. Therefore, the potential at the output terminal 107 becomes decreased to the ground potential. When the frequency of the driving signal exceeds the resonance frequency $f_r$ during the sweep control mode, the differentiating circuit 103 produces also a large differentiating output and the transistor 104 is made conductive. In this manner, the out-of range detecting circuit 102 can detect both the out-of phase lock condition and the out-of sweep range condition. It should be noted that the differentiating circuit 103 produces always the positive output signal. The remaining construction and operation of the present embodiment is entirely the same as those of the embodiment shown in FIG. 9 and therefore a detailed explanation thereof is not repeated.

In the embodiments so far explained, the sweep control mode can be positively changed into the feedback control mode. Further, when the phase lock condition is broken, the phase lock loop 37 is changed into the sweep control mode and further the abnormality of the hand piece 35 can be also detected. Moreover, since the constant current driving is adopted, the amplitude of the vibration of the hand piece 35 can be made constant and the frequency characteristic of the impedance of the ultrasonic vibrating element 36 can be simply detected by monitoring the driving voltage, so that the resonance point can be detected precisely and positively. Furthermore, the voltage applied to the ultrasonic vibrating element 36 and the current passing through the ultrasonic vibrating element are detected in a differential manner, the in-phase noise can be removed effectively and the voltage and current can be detected effectively in regardless of the output type of the power amplifier 49. As a result, in that the circuits neighboring the power amplifier can be floated from the ground potential, so that the leakage current of the patient circuit with respect to the ground can be reduced materially.

In the above explained ultrasonic surgical knife, the voltage and current are detected on the primary side of the matching transformer 38, but they may be equally detected on the secondary side of the matching transformer. Further, the frequency range of the reference signal $\theta_{ref}$ may be set to a narrower range which does not include the antiresonance frequencies $f_1$ and $f_2$ of the ultrasonic vibrating element 36. In this case, the erroneous lock-in at these antiresonance frequencies can be more positively prevented.

In the embodiments so far explained, the current level of the driving signal is changed from the lower level during the frequency sweep control mode to the higher level during the feedback control mode. In the known ultrasonic transducer driving circuit described in the above mentioned U.S. Pat. No. 4,587,958, there is provided a starting impulse reducing circuit for reducing the impulse due to the transient current upon the starting of oscillation. According to the present invention, the current level of the driving signal is reduced to the lower level during the sweep control mode and after the phase-lock operation has attained, the current level is changed to the higher level. In this case, even if the starting impulse reducing circuit is provided, when the current level is change from the lower level to the higher level abruptly, there might be produced a large variation in stress applied on the ultrasonic transducer and the transducer might be broken. Furthermore, when the current level is changed abruptly, the lock-in condition might be lost. According to further aspect of the invention, the current level is gradually increased from the lower level to the higher level when the driving signal is phase-locked with the resonance vibration of the ultrasonic vibrating element, so that the ultrasonic vibrating element can be effectively prevented from being damaged or broken and the lock-in condition is not affected by the change in the current level.

Figure 18:
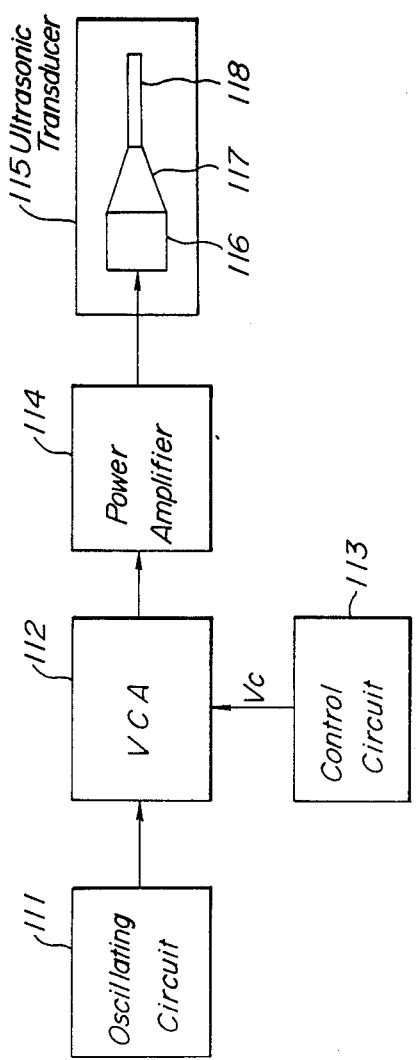
FIG. 18 is a block diagram depicting a third embodiment of the driving circuit according to the invention.

FIG. 18 is a block diagram showing an embodiment of the ultrasonic transducer driving circuit according to the invention in which the above explained protection circuit is provided. FIG. 18 shows an oscillating circuit 111 such as a voltage controlled oscillator (VCO), a voltage controlled amplifier (VCA) 112 whose amplification factor is adjusted by a control voltage applied from a control circuit 113, a power amplifier 114 for amplifying the output of the VCA, and an ultrasonic transducer 115 including an ultrasonic vibrating element 116, a hone 117 for amplifying the vibration of the element and a probe 118 connected to the hone.

Figure 19:
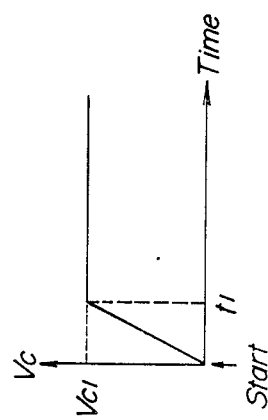
FIG. 19 is a graph showing the variation of the vibration amplitude control voltage.

When the driving circuit is ordered to be actuated, the control circuit 113 starts to generate the control voltage $V_c$ whose amplitude is gradually increased as shown by a curve illustrated in FIG. 19. That is to say, the control voltage $V_c$ is increased gradually within a predetermined time period $t_1$ and after that the control voltage is maintained at a given constant level $V_{c1}$. Then, the amplification factor of VCA 112 is also gradually increased, and the current level of the driving signal is also gradually increased, so that the amplitude of the vibration of the ultrasonic vibrating element is also increased gradually. In the manner explained above, in the present embodiment, since the current level of the driving signal is gradually increased from zero or a sufficiently small value, there is not produced a large variation in the stress applied upon the ultrasonic vibrating element 116, and therefore the ultrasonic vibrating element can be effectively protected against breakage or other damage.

Figure 20:
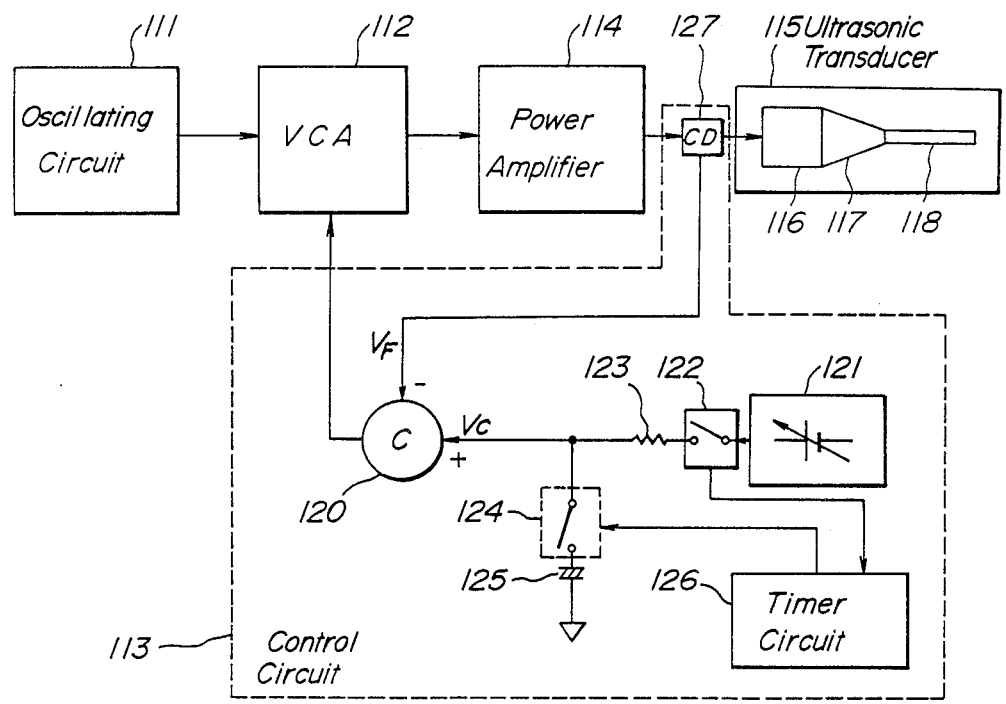
FIG. 20 is a block diagram illustrating a fourth embodiment of the driving circuit according to the invention.

FIG. 20 is a block diagram showing another embodiment of the driving circuit illustrated in FIG. 19. The control circuit 113 includes a comparator (C) 120 having a positive input terminal to which is applied a vibration amplitude presetting voltage $V_c$ from a vibration amplitude presetting circuit 121 having a variable voltage source, a start switch 122 and a resistor 123. The positive input terminal of the comparator 120 is also connected to the reference potential or ground potential by means of a relay contact 124 and a capacitor 125. When the start switch 122 is driven, a start signal is supplied to a timer circuit 126 and the timer circuit supplies a signal to a relay to close the relay contact 124 for a predetermined time period.

Between the power amplifier 114 and the ultrasonic transducer 115 there is connected a current detector (CD) 127 and an output signal $V_F$ of the current detector is applied to a negative input of the comparator 120. The comparator 120 compares the output signal $V_F$ of the current detector 127 which represents the amplitude of the current passing through the ultrasonic vibrating element 116 with the voltage $V_c$ appearing at a junction between the resistor 123 and the relay contact 124 and generates a voltage representing a difference therebetween.

The voltage thus derived is applied to the voltage controlled amplifier 112 and is multiplied with the oscillation signal supplied from the oscillating circuit 111, and the multiplied oscillation signal is supplied to the power amplifier 114.

Before driving the ultrasonic transducer 115, the amplitude of the driving current is adjusted by operating the vibration amplitude presetting circuit 121. When the start switch 122 is closed, the timer circuit 126 is driven and the relay contact 124 is closed to connect the capacitor 125 to the positive input of the comparator 120. Therefore, the resistor 123 and the capacitor 125 constitute the time constant circuit and the voltage $V_c$ applied to the positive input of the comparator 120 is gradually increased. When the predetermined time period $t_1$ has elapsed from the close of the switch 124, the timer circuit 126 opens the relay contact 124. Then, the capacitor 125 is disconnected from the resistor 123 and the voltage $V_c$ applied to the positive terminal of the comparator 120 becomes equal to the value preset by the vibration amplitude presetting circuit 121.

Figure 21A:
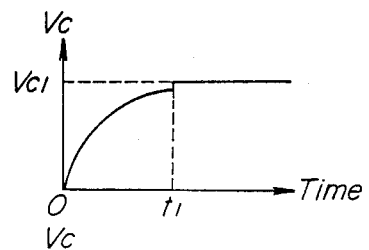
FIGS. 21A and 21B are graphs representing the variation of the control voltage.

FIG. 21A shows the variation of the voltage $V_c$ when the voltage is set to the higher level $V_{c1}$, and FIG. 20B represents the case in which the preset voltage level $V_{c2}$ is set low. In both cases, the voltage applied to the positive input terminal of the comparator 120 is gradually increased substantially to the preset levels in accordance with the time constant determined by the resistor 123 and the capacitor 125.

Figure 21B:
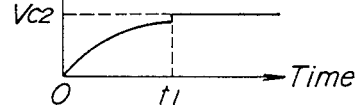

The comparator 120 compares the output voltage $V_F$ from the current detector 127 and the voltage $V_c$ with each other to derive the difference therebetween. This difference voltage is applied to the VCA 112 and its amplification factor is changed in accordance with the difference voltage such that the current of the driving signal passing through the ultrasonic vibrating element 116 is changed in accordance with the predetermined pattern similar to the curves shown in FIGS. 21A and 21B.

FIG. 22 is a block diagram showing another embodiment of the driving circuit according to the invention. In the present embodiment, there is provided a phase lock loop for adjusting the frequency of the driving signal to the resonance frequency of the ultrasonic vibrating element. An output oscillation generated from a voltage controlled oscillator 131 is applied to an ultrasonic transducer 132 by means of voltage controlled amplifier 133, power amplifier 134 and matching circuit (MC) 135.

The matching circuit 135 functions to take a matching between the driving circuit and the ultrasonic transducer so that the ultrasonic transducer can be driven efficiently. The matching circuit 135 comprises voltage phase detecting circuit (VP) 136 for detecting the phase of the driving voltage, current phase the detecting circuit (CP) 137 for detecting phase of the driving current, and current amplitude detecting circuit (CA) 138 for detecting the amplitude of the driving current. The outputs of the voltage phase detecting circuit 136 and current phase detecting circuit 137 are applied to a phase comparator (PC) 139, and the phase comparator produces the phase difference which is applied via a low pass filter (LPF) 140 to the control terminal of VCO 131 as the frequency control voltage. The control terminal of VCO 131 is connectable to the ground potential by means of a relay contact 141. As is well known in the art, the low pass filter 140 serves to remove higher order components in the frequency control voltage produced from the phase comparator 139. The phase lock loop constituted by VCO 131, voltage and current phase detecting circuits 136 and 137 in the matching circuit 135, phase comparator 139 and low pass filter 140 functions to phase-lock the driving signal with the vibration phase of the ultrasonic vibrating element 142 to which a hone 143 and a probe 144 are connected.

There are also provided a series circuit of a variable resistor 145 for presetting the minimum current level of the driving signal, a potentiometer 146 for adjusting the amplitude of the vibration of ultrasonic vibrating element and a variable resistor 147 for presetting the maximum current level of the driving signal. The maximum current level presetting variable resistor 147 is provided for presetting the maximum current value of the driving signal in order not to drive the ultrasonic vibrating element 142 excessively, so that the ultrasonic vibrating element can be protected against damage or breakage. The tap of the vibration amplitude presetting potentiometer 147 is connected to the non-inverted input of a differential amplifier 148 to whose inverted input is connected the output of the current amplitude detecting circuit 138 via a resistor 149. The output of the differential amplifier 148 is connected to its inverted input by means of a feedback resistor 150 and to the voltage controlled amplifier 133.

The tap of the potentiometer 146 is also connected to one end of a capacitor 151 via a relay contact 152 and the other end of the capacitor is connected to a junction point between the minimum current presetting variable resistor 145 and the potentiometer 146. Across the capacitor 151 is connected a series circuit of relay contact 153 and resistor 154.

There is further provided a start switch 155 which is connected to a timer circuit 156 to which are connected relays 157, 158 and 159 for driving the relay contacts 160; 141, 153; and 152, respectively.

Figure 23:
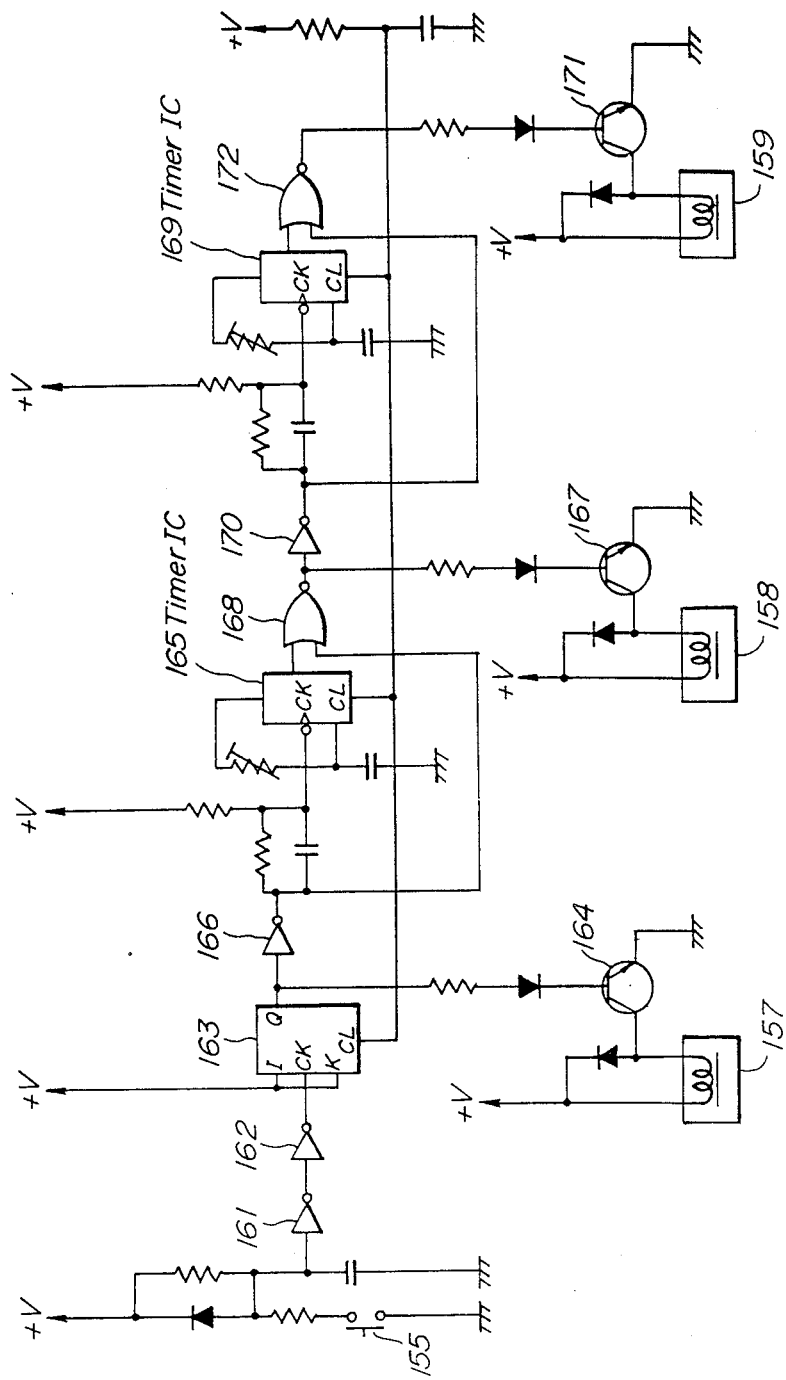
FIG. 23 is a circuit diagram of the timer circuit shown in FIG. 22.

FIG. 23 is a circuit diagram showing the detailed construction of the timer circuit 156. An output of the start switch 155 is connected via two inverters 161 and 162 to the clock terminal CK of a J-K flip-flop 163. Q output terminal of the flip-flop 163 is connected to a base of a transistor 164 as well as to the clock terminal CK of a first timer IC 165 via an inverter 166. The emitter of the transistor 164 is connected to the ground potential and the collector is connected to the relay 157. An output of the timer IC 165 is connected to a base of a transistor 167 by means of a NOR gate 168. The emitter of the transistor 167 is connected to the ground potential and the collector is connected to the relay 158.

The output of the NOR gate 168 is coupled with the clock terminal CK of a second timer IC 169 via an inverter 170. The output of the second timer IC 169 is connected to a base of a transistor 171 by means of a NOR gate 172. The emitter of the transistor 171 is connected to the ground potential and the collector is connected to the relay 159.

Figure 24:
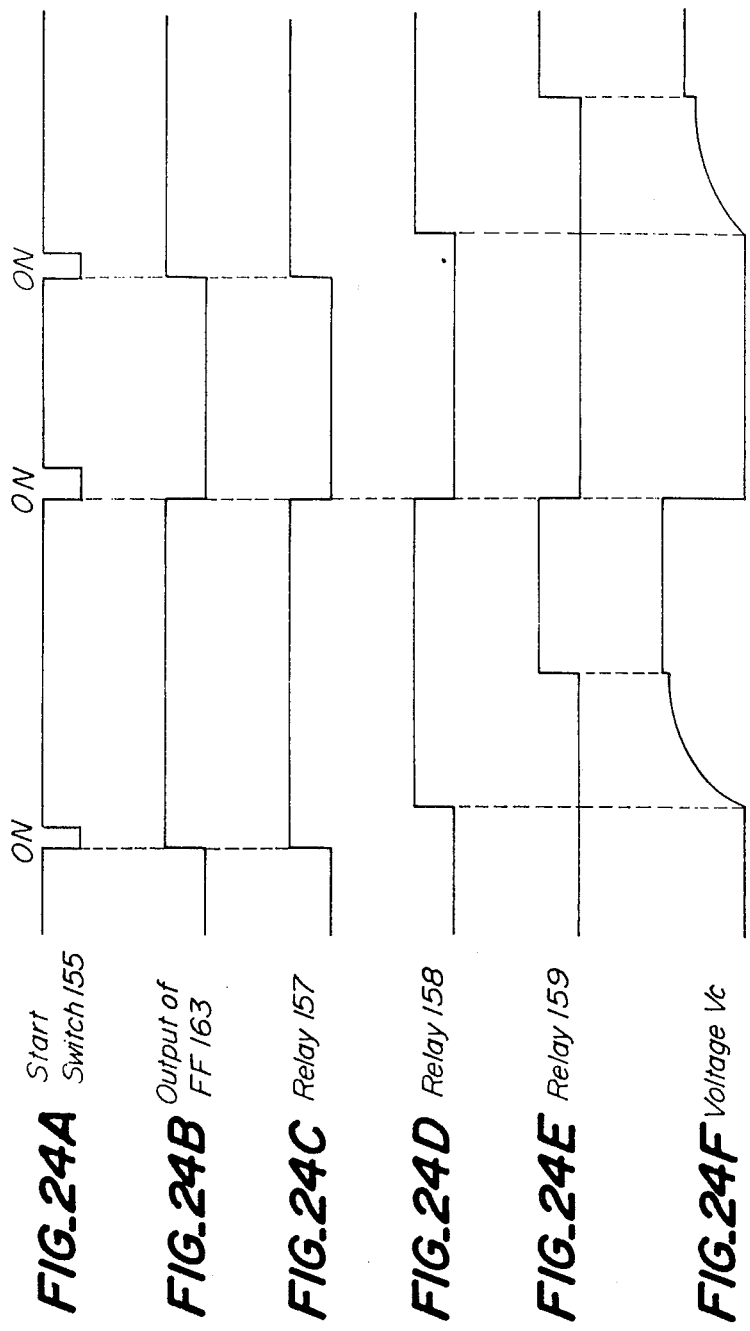
FIGS. 24A to 24F are signal waveforms for explaining the operation of the driving circuit illustrated in FIG. 22.

Now the operation of the driving circuit shown in FIG. 22 will be explained also with reference to signal waveforms illustrated in FIG. 24. Before actually driving the ultrasonic transducer 132, the minimum and maximum current presetting variable resistors 145 and 147 and the current amplitude presetting potentiometer 146 are suitably adjusted. During a time period from the power switch ON to the start switch 155 ON, none of the relays 157, 158 and 159 are energized and the input of the power amplifier 134 is connected to the ground potential via a resistor 173. Therefore, the output of the power amplifier 134 is substantially unaffected by the noise and the ultrasonic vibrating element 142 is effectively prevented from being energized erroneously. Further, the output side of the low pass filter 140 is connected to the ground potential by means of the relay circuit 141. Therefore, the voltage controlled oscillator 131 is in the self-running mode. Usually, in the self-running mode, the oscillator 131 oscillates at the middle frequency of the frequency range. The capacitor 151 is shunted by the relay contact 153 and resistor 154, and the capacitor is connected to the non-inverted input terminal of the differential amplifier 148 via the relay contact 152. Thus, the voltage $V_c$ applied to the non-inverted input of the differential amplifier 148 is equal to the voltage value which has been set by the minimum current presetting variable resistor 145.

When the start switch 155 is closed, a pulse having the low level shown in FIG. 24A is applied to the clock terminal CK of the flip-flop 163. Then, the Q output of the flip-flop 163 becomes at the high level as illustrated in FIG. 14B. Then, the relay 157 is energized as depicted in FIG. 24C to initiate the operation of the timer IC 165. When the relay 157 is operated, the relay contact 160 is driven to connect VCA 133 and power amplifier 134 with each other and the output of VCA 133 is applied to the power amplifier 134 via the relay contact 160, and the power amplifier 134 supplies, to the ultrasonic vibrating element 142, the driving signal having the constant lower current level determined by the minimum current presetting variable resistor 145. Then, the phase comparator 139 compares the phase of the voltage phase detection signal supplied from the voltage phase detecting circuit 136 and the phase of the current phase detection signal supplied from the current phase detecting circuit 137 with each other to derive the phase difference therebetween. The minimum current level presetting variable resistor 145 is adjusted such that the driving signal has a suitable amplitude for effecting the phase comparison in the phase comparator 139 in an accurate and positive manner and the ultrasonic vibrating element 142 is not subjected to the excessive impulse.

After a predetermined time period has elapsed, the output of the timer IC 165 becomes at the high level H and the relay 158 is energized as illustrated in FIG. 24D and the timer IC 169 is operated. Then, the relay contact 141 is opened and thus the output voltage of the low pass filter 140 is applied to VCO 131.

As explained above, VCO 131 constitutes the phase lock loop together with the phase comparator 139 and low pass filter 140 and the frequency of the driving signal is automatically adjusted to follow the varying resonance frequency of the ultrasonic vibrating element 142. When the relay 158 is operated, the relay contact 153 is opened, so that the voltage $V_c$ applied to the non inverted input of the differential amplifier 148 is increased gradually as shown in FIG. 24F due to the RC time constant circuit formed by the capacitor 151 and resistor 154.

After a given time period has elapsed, the output of the timer IC 169 becomes at the high level and the relay 159 is operated as illustrated in FIG. 24E. When the relay 159 is energized, the relay contact 152 is opened and the capacitor 151 is disconnected from the differential amplifier 148, and the voltage $V_c$ applied to the non-inverted input of the differential amplifier is equal to the preset constant value.

Figure 25:
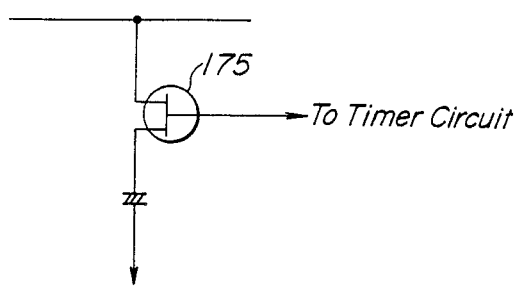
FIG. 25 is a circuit diagram of the electronic switch usable is the driving circuit shown in FIG. 22.

In the embodiments shown in FIGS. 20 and 22, the ON-OFF control for the time constant circuit is carried out by means of the relays having the mechanical contacts, but according to the invention, it is also possible to use electronic switches. One embodiment of such an electronic switch is illustrated in FIG. 25. As shown in FIG. 25, the switch is formed by a field effect transistor 175.

Figure 26:
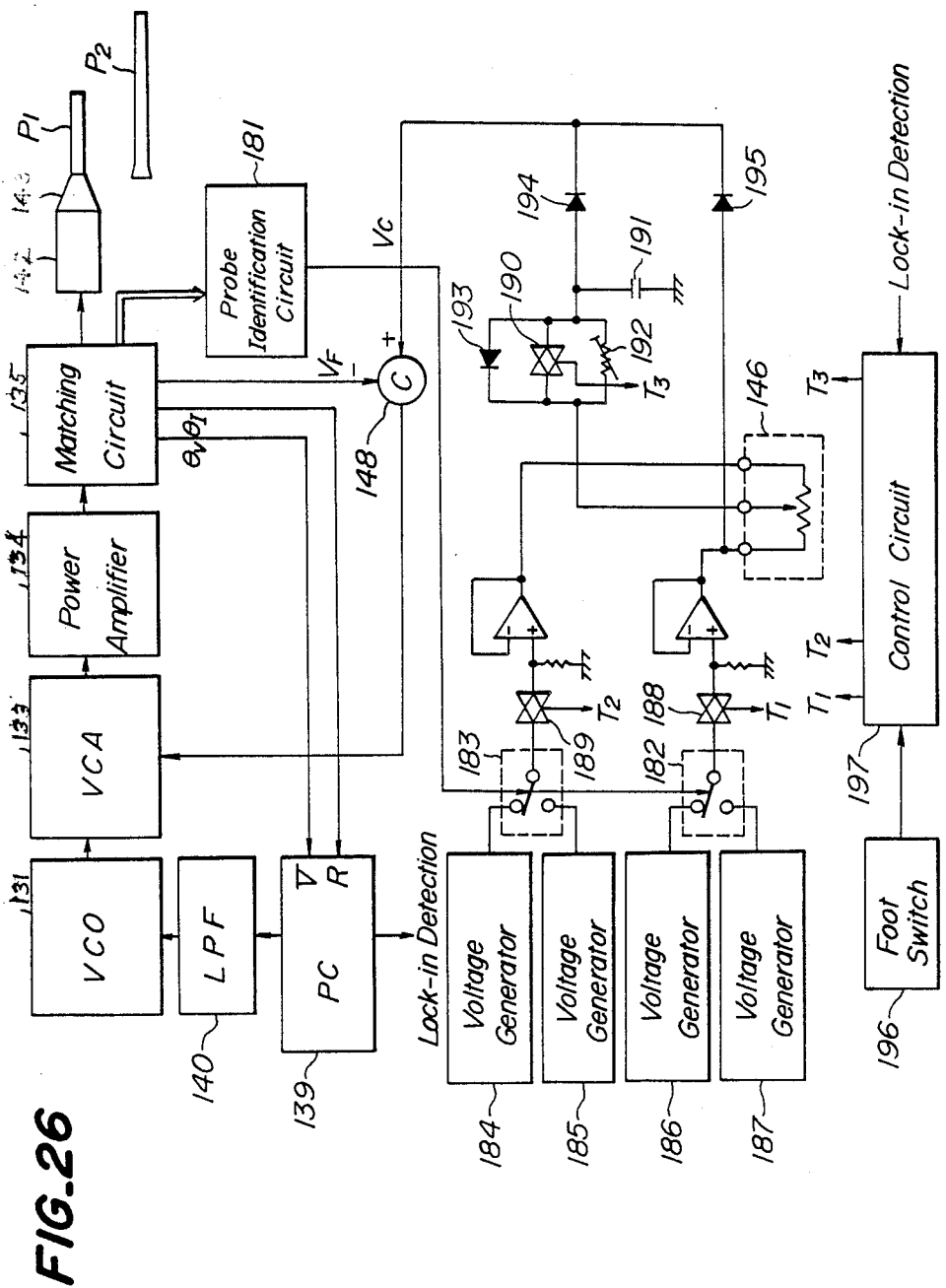
FIG. 26 is a block diagram depicting a sixth embodiment of the driving circuit according to the invention.

FIG. 26 is a block diagram depicting still another embodiment of the driving circuit according to the invention. Portions similar to those of the previous embodiment shown in FIG. 22 are denoted by the same reference numerals used in FIG. 22 as far as possible, and their detailed explanation is omitted. The ultrasonic transducer of the present embodiment may be advantageously used as the ultrasonic surgical device. The ultrasonic vibrating element 142 is coupled with a hone 143 to which different kinds of probes $P_1$ and $P_2$ can be detachably connected. There is provided a probe identification circuit 181 for detecting the kind of the probe connected to the hone 143 of the ultrasonic transducer. The probe identification circuit 181 may detect the kind of the probe by detecting the impedance of the probe or may detect information entered by manual operation with the aid of an operation panel. A probe identification signal generated from the probe identification circuit 181 is supplied to switching circuits 182 and 183. There are further arranged control voltage generating circuits 184 and 185 for generating control voltages which determine the maximum current levels of the driving signal for the probes $P_1$ and $P_2$, respectively, and control voltage generating circuits 186 and 187 for generating control voltages which determine the minimum current levels for the probes $P_1$ and $P_2$, respectively. The switching circuit 182 serves to select any one of the control voltages from the control voltage generators 186 and 187 in accordance with the probe identification signal supplied from the probe identification circuit 181, and similarly the switching circuit 183 functions to select one of the control voltages from the control voltage generating circuits 184 and 185.

There are further provided analog switches 188, 189 and 190, a capacitor 191 and a variable resistor 192 constituting the time constant circuit, a diode 193 for discharging the capacitor 191, and diodes 194 and 195 for preventing the reverse current. A foot switch 196 is connected to a control circuit 197 which generates control signals T1, T2 and T3 in response to the start signal supplied from the foot switch 196. These control signals are used to control the analog switches 188, 189 and 190, respectively. To the control circuit 197 is also supplied the phase lock detection signal from the phase comparator 139 in the phase lock loop when the frequency of the driving signal for the ultrasonic vibrating element 142 is phase-locked with the resonance frequency of the ultrasonic vibrating element 142.

Now the operation of the driving circuit shown in FIG. 26 will be explained with reference to signal waveforms illustrated in FIG. 27. In the initial condition, all the analog switches 182, 183 and 184 are made to be in the OFF mode. The probe identification circuit 181 has detected that the probe $P_1$ is coupled with the hone 143 and thus the switching circuits 182 and 183 are so driven that the control voltages for setting the minimum and maximum current levels of the driving signal for the probe $P_1$ are selectively derived. Under the above mentioned condition, when the foot switch 196 is pushed down by the operator and a foot switch signal shown in FIG. 27A is generated from the foot switch, the control signal T1 is first generated from the control circuit 197 as shown in FIG. 27B and the analog switch 188 is turned ON. Then, the minimum preset voltage value is applied to the non-inverted input of the differential amplifier 148 and the phase lock loop begins to operate in the sweep control mode and the driving signal frequency is gradually adjusted to the resonance frequency of the ultrasonic vibrating element 142. After that, the phase lock loop is driven into the feedback control mode and the driving signal is automatically adjusted to follow the resonance frequency of the ultrasonic vibrating element. When the driving signal is phase-locked with the resonance frequency of the ultrasonic vibrating element 142, the phase comparator 139 generates the lock-in detection signal as shown in FIG. 27C, said lock-in detection signal being supplied to the control circuit 197. Then, the control circuit 197 generates the control signal T2 by means of which the analog switch 189 is turned ON as illustrated in FIG. 27D. Then, the maximum and minimum current presetting voltages are applied across an amplitude presetting potentiometer 146 and the voltage on the tap of the potentiometer is applied to the time constant circuit formed by the variable resistor 192 and capacitor 191. Therefore, the output voltage of the time constant circuit is gradually increased as shown in FIG. 27F and is applied to the non-inverted input of the differential amplifier 148. After the given time period $t_1$ determined by the time constant has passed, the control circuit 197 generates the control signal T3 by means of which the analog switch 190 is turned ON and the variable resistor 192 is short-circuited. Then, the voltage on the tap of the potentiometer 146 is directly applied to the non-inverted input of the differential amplifier 148.

It should be noted that even when the variable resistor 192 is short-circuited by the analog switch 190, an extra time constant circuit is formed by the capacitor 191 and the potentiometer 146. However, the resistance value of the variable resistor 192 is set relatively large, the capacitance value of the capacitor 191 is set small, and the resistance value of the amplitude presetting potentiometer 146 is set small, so that the time constant of the extra time constant circuit can be made negligibly small.

When the foot switch 196 is opened, the analog switches 188, 189 and 190 are all turned OFF and the electrostatic charge stored in the capacitor 191 is discharged via the diode 193.

When the probe $P_1$ is exchanged by the probe $P_2$, the probe identification circuit 181 generates the probe identification signal denoting that the probe $P_2$ is connected to the hone 143. Then, the switching circuit 182 and 183 are changed by the probe identification signal and the minimum and maximum current presetting voltage generators 187 and 185 are selectively connected to the analog switches 188 and 189, respectively. The remaining operation is entirely the same as the above mentioned case.

In the embodiment just explained immediately above, the amplitude of the driving signal may be decreased gradually by using the discharge of the capacitor 191 at the timer of stopping the vibration. In this case, the analog switch 190 has to be deleted. Further, in the above embodiment, the current passing through the ultrasonic vibrating element is used to effect the amplitude control, but a vibration sensor 201 may be arranged on the ultrasonic vibrating element 142 to detect directly the vibration phase of the element as illustrated in FIG. 28.

As explained above, in the embodiments shown in FIGS. 20, 22 and 26, the impulse to the ultrasonic vibrating element upon the application of the driving voltage can be removed by gradually increasing the driving current within the range of the maximum current preset value within which the ultrasonic vibrating element can be effectively protected against the breakage. Further, in the embodiment illustrated in FIG. 22, by suitably adjusting the variable resistor 192 and the time period $t_1$, after the phase-lock condition has been attained, the lock-in condition is hardly broken or lost during the gradual increase of the amplitude of the driving signal, so that the ultrasonic vibrating element can vibrate positively and correctly.

Figure 29:
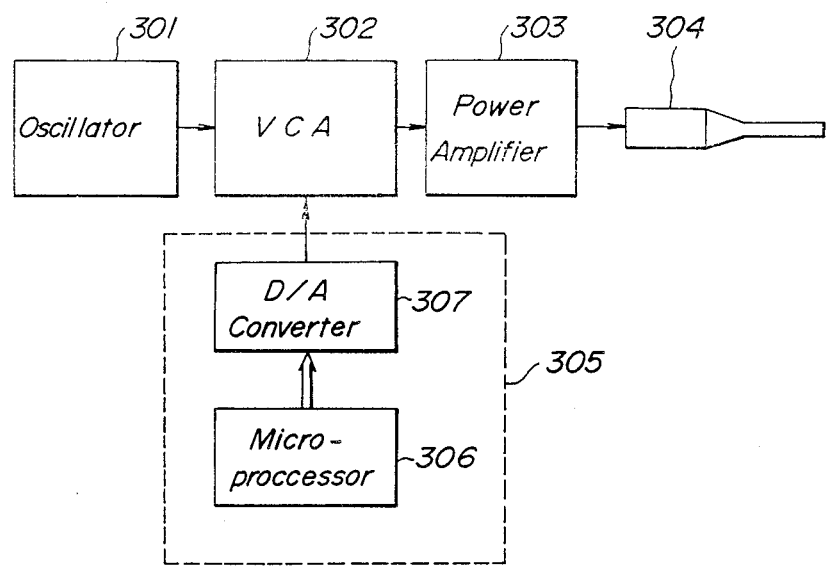
FIG. 29 is a block diagram illustrating a seventh embodiment of the driving circuit according to the invention.
Figure 30:
FIG. 30 is a graph showing the variation of the voltage for controlling the amplification of the voltage controlled amplifier shown in FIG. 29.

FIG. 29 is a block diagram showing still another embodiment of the driving circuit according to the invention. In this embodiment, an oscillation signal generated by an oscillator 301 is supplied via voltage controlled amplifier 302 and power amplifier 303 to an ultrasonic vibrating element 304. The amplification factor of VCA 302 is produced by a control circuit 305 including a microprocessor 306 and an A/D converter 307. The microprocessor 306 generates a digital signal shown in FIG. 30 and this digital signal is converted into the analog signal by means of the A/D converter 307. As illustrated in FIG. 30, the digital signal generated from the microprocessor 306 is increased in a stepwise manner until a predetermined time $t_1$ and then is constant constant. Therefore, the amplitude of the driving signal generated from the VCA 302 is changed accordingly. In this manner, also in the present embodiment, the vibration amplitude of the ultrasonic vibrating element 304 is gradually increased within the predetermined time period $t_1$.

In the present embodiment, the shape of the increase in the amplitude of the vibration of the ultrasonic vibrating element 304 can be simply set or changed by changing the software in the microprocessor 306, so that the whole system can be simplified and the adjustment can be performed easily.

FIG. 31 is a block diagram showing still another embodiment of the driving circuit according to the invention. The driving circuit of the present embodiment is a combination of the two embodiments illustrated in FIGS. 3 and 26, so that portions similar to those of these embodiments are denoted with the same reference numerals used in FIGS. 3 and 26. In the present embodiment, between the power amplifier 13 and the ultrasonic transducer 10 is connected a voltage and current detecting circuit 310 for detecting the voltage phase signal $\theta_v$, current phase signal $\theta_I$, absolute value of voltage $|V|$ and absolute value of current $|I|$. Since the driving circuit operates in the constant current mode, the absolute voltage value $|V|$ represents the impedance $|Z|$ of the ultrasonic transducer 10, so that this absolute voltage value is applied to the resonance point detecting circuit 22 as well as to the probe identification circuit 181. The probe identification circuit 181 detects the kind of a probe $P_1$ or $P_2$ connected to the hone 143. The resonance point detecting circuit 22 produces the output signal when the driving signal is in-phase with the resonance vibration of the ultrasonic vibrating element 142, so that this output signal is supplied to the control circuit 197 as the lock-in detection signal. In the present embodiment, the kind of the probe $P_1$ is identified by detecting the impedance of the ultrasonic transducer 10 and the switches 182 and 183 are driven by the output of the probe identification circuit 181 to select the minimum and maximum current control voltages corresponding to the detected kind of the probe. Further, during the sweep control mode, the switching circuit 18 is driven in the position shown in FIG. 31 and the reference signal $\theta_{ref}$ produced by the reference signal generating circuit 19 is supplied to the phase comparator 15 together with the voltage phase signal $\theta_v$. Then, the frequency of the driving signal is gradually increased in accordance with the frequency of the reference signal. During this sweep control mode, the current level of the driving signal is maintained to be lower than the predetermined small value preset by the control voltage generator 186. When the driving signal is locked with the vibration phase of the ultrasonic vibrating element 142 at its resonance frequency $f_r$, the resonance point detecting circuit 22 produces the in-phase signal by means of which the switch circuit 18 is changed and at the same time, the control circuit 197 generates the control signal $T_2$. Then, the control voltage generated by the control voltage generator 184 is applied to the time constant circuit formed by the capacitor 191 and variable resistor 192, and the amplitude of the driving current is gradually increased up to the maximum current value determined by the control voltage of the voltage generator 184 and the potentiometer 146.

The present invention is not limited to the embodiments explained above, but many modifications and alternatives may be conceived by those skilled in the art so as to be within the scope of the invention.

What is claimed is:

1. A circuit for driving an ultrasonic transducer comprising
    an oscillating means for generating a driving signal whose frequency is controlled in accordance with a frequency control signal;
    a first phase detecting means for detecting a phase of said driving signal to generate a first phase detection signal;
    a second phase detecting means for detecting a phase of the vibration of the ultrasonic transducer to generate a second phase detection signal;
    a reference signal generating means for generating a reference signal whose frequency is continuously changed; and
    a frequency control means for selectively changing the operation of the driving circuit between a sweep control mode in which the frequency of the driving signal generated from said oscillating means is controlled to follow the frequency of said reference signal by comparing one of said first and second phase detection signals with said reference signal and a feedback control mode in which the frequency of the driving signal generated from said oscillating means is controlled to follow a resonance frequency of the ultrasonic transducer by comparing said first and second phase detection signals with each other.

2. A driving circuit according to claim 1, wherein said frequency control means comprises a resonance point detecting circuit for detecting such a condition that the driving signal is phase-locked with the vibration of the ultrasonic transducer which is vibrated at its resonance frequency and producing a resonance point detection signal, and a switching circuit for changing the operation mode of the driving circuit between the sweep control mode and the feedback control mode in response to said resonance point detection signal.

3. A driving circuit according to claim 2, wherein said frequency controlling means further comprises a phase comparator having a reference input terminal, a variable input terminal and an output terminal, said reference input terminal being connected to an output terminal of said said switching circuit, and said variable input terminal being connected to an output terminal of the other of said first and second phase detecting means, and said oscillating means comprises a voltage controlled oscillator having a control input terminal coupled with said output terminal of said phase comparator, whereby said phase comparator and voltage controlled oscillator constitute a phase lock loop in which the phase difference between said first and second phase detection signals is detected by said phase comparator and an oscillation frequency of the voltage controlled oscillator is controlled in accordance with said phase difference so that the frequency of the driving signal is automatically adjusted to follow the resonance frequency of said ultrasonic transducer.

4. A driving circuit according to claim 3, wherein said frequency controlling means further comprises a loop filter connected between said output terminal of the phase comparator and the control input terminal of the voltage controlled oscillator and having the integrating function for integrating a phase difference derived from said phase comparator.

5. A driving circuit according to claim 3, wherein said first phase detecting means comprises a voltage phase detector for detecting the phase of a voltage of the driving signal, and said second phase detecting means comprises a current phase detector for detecting the phase of a current of the driving signal.

6. A driving circuit according to claim 3, wherein said first phase detecting means comprises a voltage phase detector for detecting the phase of a voltage of the driving signal, and said second phase detecting means comprises a vibration sensor applied on the ultrasonic transducer for detecting the vibration of the ultrasonic transducer.

7. A driving circuit according to claim 2, wherein said resonance point detecting circuit comprises an impedance detector for detecting an impedance of the ultrasonic transducer and generating an enabling signal when the impedance of the ultrasonic transducer is reduced below a predetermined threshold level, and a phase comparator which is enabled in response to said enabling signal to initiate to compare the phases of said first and second phase detection signals with each other and produce said resonance point detection signal when a phase difference between said phases becomes zero.

8. A driving circuit according to claim 7, wherein the driving circuit further comprises a means for keeping constant an amplitude of a current of the driving signal, and said impedance detector comprises an absolute value detecting circuit for detecting an absolute value of a voltage of said driving signal and a voltage comparator for comparing the absolute value of the voltage of the driving signal with a predetermined threshold value which corresponds to said predetermined threshold level, said enabling signal being generated when the absolute value of the voltage of the driving signal becomes smaller than said predetermined threshold value.

9. A driving circuit according to claim 8, wherein said means for keeping constant the amplitude of the current of the driving signal comprises a voltage controlled amplifier for amplifying the driving signal and having a control input terminal, an absolute value detector for detecting an absolute value of the current of the driving signal, a presetting means for generating a control voltage corresponding to said predetermined threshold value, and a differential amplifier for deriving a difference between said absolute value of the current and said control voltage, whereby said difference is applied to said control input terminal of the voltage controlled amplifier to change an amplification factor thereof such that the amplitude of the current of the driving signal is kept to said predetermined threshold level.

10. A driving circuit according to claim 3, wherein said frequency controlling means further comprises an out-of range detector for producing a reset signal by detecting a condition in which the frequency of the driving signal is changed beyond a predetermined frequency range, and a control circuit for driving said switching circuit in response to said reset signal such that the frequency controlling means is operated in the sweep control mode when said reset signal is generated.

11. A driving circuit according to claim 10, wherein said out-of range detector comprises a window comparator for comparing said phase difference generated by the phase comparator with upper and lower threshold levels and producing said reset signal when the phase difference is changed beyond said upper and lower threshold levels.

12. A driving circuit according to claim 10, wherein said out-of range detector comprises an absolute value detector for detecting an absolute value of the voltage of the driving signal, a differentiating circuit for differentiating the absolute value of the voltage of the driving signal, and a gate circuit for generating said reset signal when said differentiating circuit generates a large output signal.

13. A driving circuit according to claim 10, wherein said frequency controlling means further comprises a counter for counting the reset signals and generating an abnormality indication signal when the number of the reset signals exceeds a predetermined number.

14. A driving circuit according to claim 1, wherein said reference signal generating means is constructed such that the frequency of the reference signal is varied monotonously.

15. A circuit for driving an ultrasonic transducer and including a driving signal generating means which has an open loop control mode in which the frequency of the driving signal is increased or decreased continuously and a feedback control mode in which the frequency of the driving signal is controlled in accordance with a phase difference between voltage and current of the driving signal such that the frequency of the driving signal follows a varying resonance frequency of the ultrasonic transducer, and a switching means for selectively driving said driving signal generating means between said open loop control mode and the feedback control mode by comparing the phases of the voltage and current of the driving signal, the improvement being characterized in that said switching means comprises an impedance detector for detecting an impedance of the ultrasonic transducer, a comparator for comparing the impedance of the ultrasonic transducer with a predetermined threshold value and generating a resonance point detecting signal when the impedance is decreased below said threshold value, and a switch for changing the open loop control mode into the feedback control mode in response to said resonance point detection signal.

16. A driving circuit according to claim 15, wherein the driving signal generating means comprises a means for keeping constant an amplitude of a current of the driving signal, and said impedance detector comprises an absolute value detecting circuit for detecting an absolute value of a voltage of said driving signal and a voltage comparator for comparing the absolute value of the voltage of the driving signal with a predetermined threshold value which corresponds to said predetermined threshold level, said enabling signal being generated when the absolute value of the voltage of the driving signal becomes smaller than said predetermined threshold value.

17. A driving circuit according to claim 16, wherein said means for keeping constant the amplitude of the current of the driving signal comprises a voltage controlled amplifier for amplifying the driving signal and having a control input terminal, an absolute value detector for detecting an absolute value of the current of the driving signal, a presetting means for generating a control voltage corresponding to said predetermined threshold value, and a differential amplifier for deriving a difference between said absolute value of the current and said control voltage, whereby said difference is applied to said control input terminal of the voltage controlled amplifier to change an amplification factor thereof such that the amplitude of the current of the driving signal is kept to said predetermined threshold level.

18. A driving circuit according to claim 17, wherein said impedance detector comprises an absolute value detecting circuit for detecting an absolute value of a voltage of said driving signal and a voltage comparator for comparing the absolute value of the voltage of the driving signal with a predetermined threshold value which corresponds to said predetermined threshold level, said open loop control mode is changed into said feedback control mode when the absolute value of the voltage of the driving signal becomes smaller than said predetermined threshold value.

19. A driving circuit according to claim 15, wherein said driving signal generating means further comprises an out-of range detector for producing a reset signal by detecting a condition in which the frequency of the driving signal is shifted from the resonance frequency of the ultrasonic transducer to such an extent that the frequency of the driving signal could be no more adjusted to follow the resonance frequency, and a control circuit for driving said switching circuit in response to said reset signal such that the driving signal generating means is operated in the open loop control mode when said reset signal is generated.

20. A driving circuit according to claim 19, wherein said out-of range detector is constructed such that said reset signal is generated when the frequency of the driving signal is changed beyond a predetermined frequency range.

21. A driving circuit for generating a driving signal for an ultrasonic transducer including
 a frequency sweep means for effecting the frequency sweep over a predetermined frequency range;
 a means for operating the driving circuit under a sweep control mode in which the frequency of the driving signal is increased or decreased continuously within said predetermined frequency range with the aid of said frequency sweep means;
 a means for operating the driving circuit under a feedback control mode in which the frequency of the driving signal is controlled to follow a varying resonance frequency of the ultrasonic transducer; and
 a switching means for selectively driving said driving circuit between said sweep control mode and the feedback control mode by comparing the phases of the voltage and current of the driving signal, the improvement being characterized in that said switching means comprises an impedance detector for detecting an impedance of the ultrasonic transducer, a comparator for comparing the impedance of the ultrasonic transducer with a predetermined threshold value and generating a resonance point detection signal when the impedance is decreased below said threshold value, and a switching circuit for changing the sweep control mode into the feedback control mode in response to said resonance point detection signal.

22. A driving circuit according to claim 21, wherein said means for operating the driving circuit under the sweep control mode and feedback control mode comprises a phase lock loop including a voltage controlled oscillator having a frequency control terminal and a phase comparator for comparing a phase of the driving signal and a vibration phase of the ultrasonic transducer, said frequency sweep means comprises a reference signal generating circuit for generating a reference signal whose frequency is varied continuously, and said switching means is so constructed that in the sweep control mode, the reference signal is supplied to said phase comparator and in the feedback control mode, a signal for representing the phase of the vibration of the ultrasonic transducer is supplied to said phase comparator.

23. A driving circuit according to claim 22, wherein said signal for representing the phase of the vibration of the ultrasonic transducer is generated from a circuit for detecting a phase of a current of the driving signal passing through the ultrasonic transducer.

24. A driving circuit according to claim 22, wherein said signal for representing the phase of the vibration of the ultrasonic transducer is generated from a vibration sensor arranged on the ultrasonic transducer.

25. A driving circuit according to claim 21, wherein the driving circuit further comprises a means for keeping constant an amplitude of a current of the driving signal, and said impedance detector comprises an absolute value detecting circuit for detecting an absolute value of a voltage of said driving signal and a voltage comparator for comparing the absolute value of the voltage of the driving signal with a predetermined threshold value which corresponds to said predetermined threshold value.

26. A driving circuit according to claim 25, wherein said means for keeping constant the amplitude of the current of the driving signal comprises a voltage controlled amplifier for amplifying the driving signal and having a control input terminal, an absolute value detector for detecting an absolute value of the current of the driving signal, a presetting means for generating a control voltage corresponding to said predetermined threshold value, and a differential amplifier for deriving a difference between said absolute value of the current and said control voltage, whereby said difference is applied to said control input terminal of the voltage controlled amplifier to change an amplification factor thereof such that the amplitude of the current of the driving signal is kept to said predetermined threshold level.

27. A driving circuit according to claim 26, wherein said impedance detector comprises an absolute value detecting circuit for detecting an absolute value of a voltage of said driving signal and a voltage comparator for comparing the absolute value of the voltage of the driving signal with a predetermined threshold value which corresponds to said predetermined threshold value, said open loop control mode is changed into said feedback control mode when the absolute value of the voltage of the driving signal becomes smaller than said predetermined threshold value.

28. A driving circuit for generating a driving signal for an ultrasonic transducer comprising
   a phase lock loop for adjusting a frequency of the driving signal to follow a resonance frequency of the ultrasonic transducer in accordance with a voltage phase detection signal representing a phase of a voltage of the driving signal and a current phase detection signal;
   a reference signal generating circuit for generating a reference signal having a frequency which is varied continuously; and
   a control means for selectively driving said phase lock loop between a first control mode in which during a start period, the frequency of the driving signal is controlled in accordance with a phase difference between the reference signal and the voltage phase detection signal until the driving signal is phase-locked with a resonance frequency of the ultrasonic transducer, and a second control mode in which after the driving signal has been phase-locked with the resonance frequency of the ultrasonic transducer, the frequency of the driving signal is controlled in accordance with a phase difference between the voltage phase detection signal and the current phase detection signal.

29. A driving circuit according to claim 28, wherein said frequency of the reference signal is changed monotonously.

30. A driving circuit according to claim 29, wherein said control means comprises a resonance point detecting means for generating a resonance point detection signal when the driving signal is phase-locked with the resonance frequency of the ultrasonic transducer, and a switching circuit for responding to said resonance point detection signal to change the operation of the driving circuit from the first control mode to the second control model.

31. A driving circuit according to claim 30, further comprising a current control means for keeping constant an amplitude of the current of the driving signal.

32. A driving circuit according to claim 31, wherein said current control means is constructed such that during the first control mode, the amplitude of the level, and during the second control mode the amplitude of the current of the driving signal is set to a higher current level.

33. A driving circuit according to claim 32, wherein said current control means further comprises a means for adjusting said lower current level and higher current lever.

34. A driving circuit according to claim 32, wherein said current control means comprises a plurality of lower current level presetting circuits, a plurality of higher current level presetting circuits, a detector for detecting a kind of a probe installed in the ultrasonic transducer to produce a probe identification signal, and a switching means for selectively connecting one of said plurality of the lower current presetting circuits and one of said plurality of the higher current level presetting circuits in accordance with said probe identification signal.

35. A driving circuit according to claim 34, wherein said probe identification signal is constructed such that the kind of the probe is identified by detecting an impedance of the ultrasonic transducer.

36. A driving circuit according to claim 32, wherein said current control means further comprises a limiting means for limiting the amplitude of the current of the driving signal.

37. A driving circuit for driving an ultrasonic transducer comprising
   a frequency sweep means for effecting the frequency sweep over a predetermined frequency range;
   a means for operating the driving circuit under a sweep control mode in which the frequency of the driving signal is increased or decreased continuously within said predetermined frequency range with the aid of said frequency sweep means;
   a means for operating the driving circuit under a feedback control mode in which the frequency of the driving signal is controlled to follow a varying resonance frequency of the ultrasonic transducer;
   a switching means for selectively driving said driving circuit between said sweep control mode and the feedback control mode;
   a means for amplifying the driving signal with a variable amplification factor; and
   an amplification control means for controlling the amplification factor of said amplifying means such that the amplification factor is gradually increased from a lower value during the sweep control mode to a higher value during the feedback control mode.

38. A driving circuit according to claim 37, wherein said amplifying means comprises a voltage controlled amplifier whose amplification factor is controlled by a control voltage applied to a control input terminal thereof, and said amplification control means comprises a first voltage source means for generating a lower control voltage corresponding to said lower value of the amplification factor, a second voltage source means for generating a higher control voltage corresponding to said higher value of the amplification factor, and a time constant circuit connectable to an output of said second voltage source means to increase gradually the control voltage from the lower value to the higher value in accordance with a time constant of the time constant circuit.

39. A driving circuit according to claim 37, wherein said amplifying means comprises a voltage controlled amplifier whose amplification factor is controlled by a control voltage applied to a control input terminal thereof, and said amplification control means comprises a microprocessor for generating a gradually increasing amplification control signal and an analog-digital converter for converting the amplification control signal into an analog control voltage whose amplitude is gradually increased.

40. A driving circuit according to claim 38, wherein said first voltage source means includes a plurality of voltage sources for generating different lower control voltages, said second voltage source means includes a plurality of voltage sources for generating different higher control voltages, a means for detecting a kind of a probe installed in the ultrasonic transducer to generate a probe identification signal, and a switching means for selectively applying one of said plurality of the lower control voltages and one of said plurality of the higher control voltages to the control input terminal of the voltage controlled amplifier in accordance with said probe identification signal.

41. A driving circuit according to claim 40, wherein said probe identification signal is constructed such that the kind of the probe is identified by detecting an impedance of the ultrasonic transducer.

* * * * *